US012770292B2

(12) United States Patent
Dutta et al.

(10) Patent No.: US 12,770,292 B2
(45) Date of Patent: Oct. 20, 2026

(54) HYBRID 3D-TO-2D SLICE-WISE OBJECT LOCALIZATION ENSEMBLES

(71) Applicant: GE Precision Healthcare LLC, Waukesha, WI (US)

(72) Inventors: Sandeep Dutta, Celebration, FL (US); Christopher Philip Bridge, Somerville, MA (US); Charles Jiali Lu, Boston, MA (US); Mitchel B Harris, Brookline, MA (US); Bharti Khurana, Brookline, MA (US); Praveer Singh, Denver, CO (US); Mehak Aggarwal, San Jose, CA (US); Sujay Shivanand Kakarmath, Reading, PA (US); Ashwin Vaswani, Pittsburgh, PA (US); Amy Deubig, Dousman, WI (US); Saad Sirohey, Pewaukee, WI (US); Jayashree Kalpathy-Cramer, Morrison, CO (US)

(73) Assignees: GE PRECISION HEALTHCARE LLC, Waukesha, WI (US); Mass General Brigham Incorporated, Somerville, MA (US); The General Hospital Corporation, Boston, MA (US); The Brigham and Women's Hospital, Inc., Boston, MA (US)

( * ) Notice: Subject to any disclaimer, the term of this patent is extended or adjusted under 35 U.S.C. 154(b) by 407 days.

(21) Appl. No.: 18/450,196

(22) Filed: Aug. 15, 2023

(65) Prior Publication Data

US 2025/0061605 A1 Feb. 20, 2025

(51) Int. Cl.
*G06T 7/73* (2017.01)
*G06T 7/00* (2017.01)
(Continued)

(52) U.S. Cl.
CPC .............. *G06T 7/75* (2017.01); *G06T 7/0014* (2013.01); *G16H 30/40* (2018.01); *G16H 50/50* (2018.01);
(Continued)

(58) Field of Classification Search
CPC ..... G06T 7/75; G06T 7/0014; G06T 2200/04; G06T 2207/10081; G06T 2207/10088;
(Continued)

(56) References Cited

U.S. PATENT DOCUMENTS 11,341,639 B2 5/2022 Nicolaes
11,816,185 B1 * 11/2023 Roth ........................ G06N 3/08
(Continued)

FOREIGN PATENT DOCUMENTS

WO 2022139246 A1 6/2022

OTHER PUBLICATIONS

A. Basher, B. C. Kim, K. H. Lee and H. Y. Jung, "Volumetric Feature-Based Alzheimeras Disease Diagnosis From sMRI Data Using a Convolutional Neural Network and a Deep Neural Network," in IEEE Access, vol. 9, pp. 29870-29882, 2021 (Year: 2021).*
(Continued)

*Primary Examiner* — Atiba O Fitzpatrick
(74) *Attorney, Agent, or Firm* — Amin, Turocy & Watson, LLP

(57) ABSTRACT

Systems or techniques that facilitate hybrid 3D-to-2D slice-wise object localization ensembles are provided. In various embodiments, a system can access at least one three-dimensional voxel array. In various aspects, the system can localize, via execution of a deep learning ensemble, an object depicted in the at least one three-dimensional voxel array. In various instances, the deep learning ensemble can receive as input the at least one three-dimensional voxel array. In
(Continued)

various cases, the deep learning ensemble can produce as output a set of two-dimensional object location indicators respectively corresponding to a set of two-dimensional slices of the at least one three-dimensional voxel array.

20 Claims, 12 Drawing Sheets

(51) Int. Cl.
*G16H 30/40* (2018.01)
*G16H 50/50* (2018.01)

(52) U.S. Cl.
CPC *G06T 2200/04* (2013.01); *G06T 2207/10081* (2013.01); *G06T 2207/10088* (2013.01); *G06T 2207/10104* (2013.01); *G06T 2207/10116* (2013.01); *G06T 2207/20081* (2013.01); *G06T 2207/20084* (2013.01); *G06T 2207/20092* (2013.01); *G06T 2207/30012* (2013.01)

(58) Field of Classification Search
CPC . G06T 2207/10104; G06T 2207/10116; G06T 2207/20081; G06T 2207/20084; G06T 2207/20092; G06T 2207/30012; G06T 2207/10072–10112; G06T 7/70; G16H 30/40; G16H 50/50; G06N 20/20
See application file for complete search history.

(56) References Cited

U.S. PATENT DOCUMENTS

| | | | | |
|---|---|---|---|---|
| 11,836,921 | B2 * | 12/2023 | Oliveira Ferreira .. | G06T 7/0016 |
| 2019/0180409 | A1 * | 6/2019 | Moloney ................ | G05D 1/617 |
| 2020/0160515 | A1 | 5/2020 | Chabin et al. | |
| 2020/0160982 | A1 | 5/2020 | Gurson et al. | |
| 2020/0327660 | A1 | 10/2020 | Katouzian et al. | |
| 2020/0364856 | A1 | 11/2020 | Nicolaes | |
| 2021/0015560 | A1 | 1/2021 | Boddington et al. | |
| 2021/0097678 | A1 | 4/2021 | Dutta et al. | |
| 2021/0125707 | A1 * | 4/2021 | Rusko ....................... | G06T 7/11 |
| 2021/0216822 | A1 * | 7/2021 | Paik ........................ | G10L 15/22 |
| 2021/0346091 | A1 | 11/2021 | Haslam et al. | |
| 2021/0378616 | A1 | 12/2021 | Chan et al. | |
| 2022/0026556 | A1 * | 1/2022 | Spata ..................... | G06V 20/52 |
| 2022/0198213 | A1 * | 6/2022 | Kim ....................... | G06N 3/098 |
| 2022/0222812 | A1 * | 7/2022 | Li .......................... | G06N 3/045 |
| 2022/0233160 | A1 * | 7/2022 | Cao ...................... | G06N 3/0464 |
| 2022/0378395 | A1 * | 12/2022 | Yang ...................... | G06V 10/25 |
| 2022/0414882 | A1 * | 12/2022 | Chmelevskii Petrovich ............... | G06V 10/82 |
| 2024/0112776 | A1 * | 4/2024 | Paik ........................ | G06F 18/41 |

OTHER PUBLICATIONS

Pan, Dan; Zeng, An; Jia, Longfei; Huang, Yin; Frizzell, Tory; Song, Xiaowei, âEarly Detection of Alzheimerâs Disease Using Magnetic Resonance Imaging: A Novel Approach Combining Convolutional Neural Networks and Ensemble Learningâ, Frontiers in Neuroscience, 14, 259, May 13, 2020 (Year: 2020).*

Lin, Ts-Y et al. | “Focal Loss for Dense Object Detection.” arXiv: 1708.02002v2 [cs.CV] Feb. 7, 2018, 10 pages.

Yang, J et al. | “Reinventing 2D Convolutions for 3D Images.” arXiv: 1911.10477v4 [eess.IV] Jan. 4, 2021, 12 pages.

Non-Final Office Action received for U.S. Appl. No. 16/587,923 dated Apr. 27, 2021, 27 pages.

Burns, J.E et al. | “Automated Detection, Localization, and Classification of Traumatic Vertebral Body Fractures in the Thoracic and Lumbar Spine at CT”. Radiology 278.1 (2016): 64-73, 10 pages.

Roth et al. | “Deep convolutional networks for automated detection of posterior-element fractures on spine CT.” Medical Imaging 2016: computer-aided diagnosis. vol. 9785P (Mar. 24, 2016), doi:10.1117/12.2217146, 8 pages.

Final Office Action received for U.S. Appl. No. 16/587,923 dated Oct. 20, 2021, 29 pages.

Kellam, J. F. et al. | “Fracture and Dislocation Classification Compendium-2018.” Journal of Orthop Traums, Vo. 32, No. 1 Supplementa, Jan. 2018, 10 pages.

Non-Final Office Action received for U.S. Appl. No. 16/587,923 dated Feb. 2, 2022, 37 pages.

Al Arif, S.M.M.R et al. | “Shape-Aware Deep Convolutional Neural Network for Vertebrae Segmentation.” International Workshop on Computational Methods and Clinical Applications in Musculoskeletal Imaging, Springer, Cham, 2017, 13 pages.

Lindsey, R. et al. | “Deep neural network improves fracture detection by clinicians.” Proceedings of the National Academy of Sciences 115.45 (2018): 1159111596, 7 pages.

Raghavendra, U. et al. | “Automated system for teh detection of thoracolumbar fractures using a CNN architecture.” Future Generation Computer Systems 85 (2018): 184-189, 6 pages.

Al-Saudi, K. et al. | “The application of machine learning techniques towards the detection of fractures in CT-scans of the cervical spine.” 16th SC@RUG 2018-2019: 99, year 2019, 6 pages.

Final Office Action received for U.S. Appl. No. 16/587,923 dated May 17, 2022, 35 pages.

Whitehead, W et al. | “A Deep Approach to Spine Segmentation Using a Feed-Forward Chain of Pixel-Wise Convolutional Networks.” 2018 IEEE 15th International Symposium on Biomedical Imaging (ISBI 2018), Apr. 4-7, 2018, Washington D.C., USA, 4 pages.

* cited by examiner

HYBRID 3D-TO-2D SLICE-WISE OBJECT LOCALIZATION ENSEMBLES

TECHNICAL FIELD

The subject disclosure relates generally to object localization, and more specifically to hybrid 3D-to-2D slice-wise object localization ensembles.

BACKGROUND

A three-dimensional voxel array can depict an object. A deep learning neural network can be trained to localize that object. Existing techniques either: cause the deep learning neural network to achieve a high localization accuracy at the expense of excessive consumption of computational resources; or cause the deep learning neural network to consume fewer computational resources at the expense of deteriorated inferencing accuracy.

Accordingly, systems or techniques that can cause the deep learning neural network to consume fewer computational resources without suffering deterioration of localization accuracy can be desirable.

SUMMARY

The following presents a summary to provide a basic understanding of one or more embodiments. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, devices, systems, computer-implemented methods, apparatus or computer program products that facilitate hybrid 3D-to-2D slice-wise object localization ensembles are described.

According to one or more embodiments, a system is provided. The system can comprise a non-transitory computer-readable memory that can store computer-executable components. The system can further comprise a processor that can be operably coupled to the non-transitory computer-readable memory and that can execute the computer-executable components stored in the non-transitory computer-readable memory. In various embodiments, the computer-executable components can comprise an access component that can access at least one three-dimensional voxel array. In various aspects, the computer-executable components can comprise a model component that can localize, via execution of a deep learning ensemble, an object depicted in the at least one three-dimensional voxel array. In various instances, the deep learning ensemble can receive as input the at least one three-dimensional voxel array and can produce as output a set of two-dimensional object location indicators respectively corresponding to a set of two-dimensional slices of the at least one three-dimensional voxel array.

According to one or more embodiments, a computer-implemented method is provided. In various embodiments, the computer-implemented method can comprise accessing, by a device operatively coupled to a processor, at least one three-dimensional voxel array. In various aspects, the computer-implemented method can comprise localizing, by the device and via execution of a deep learning ensemble, an object depicted in the at least one three-dimensional voxel array. In various instances, the deep learning ensemble can receive as input the at least one three-dimensional voxel array and can produce as output a set of two-dimensional object location indicators respectively corresponding to a set of two-dimensional slices of the at least one three-dimensional voxel array.

According to one or more embodiments, a computer program product for facilitating hybrid 3D-to-2D slice-wise object localization ensembles is provided. In various embodiments, the computer program product can comprise a non-transitory computer-readable memory having program instructions embodied therewith. In various aspects, the program instructions can be executable by a processor to cause the processor to access at least one three-dimensional voxel array depicting a cervical spine of a medical patient. In various instances, the program instructions can be further executable to cause the processor to localize, via execution of a deep learning ensemble, a fracture in the cervical spine. In various cases, the deep learning ensemble can receive as input the at least one three-dimensional voxel array and can produce as output a set of two-dimensional fracture location indicators respectively corresponding to a set of two-dimensional slices of the at least one three-dimensional voxel array.

DETAILED DESCRIPTION

Figure 1:
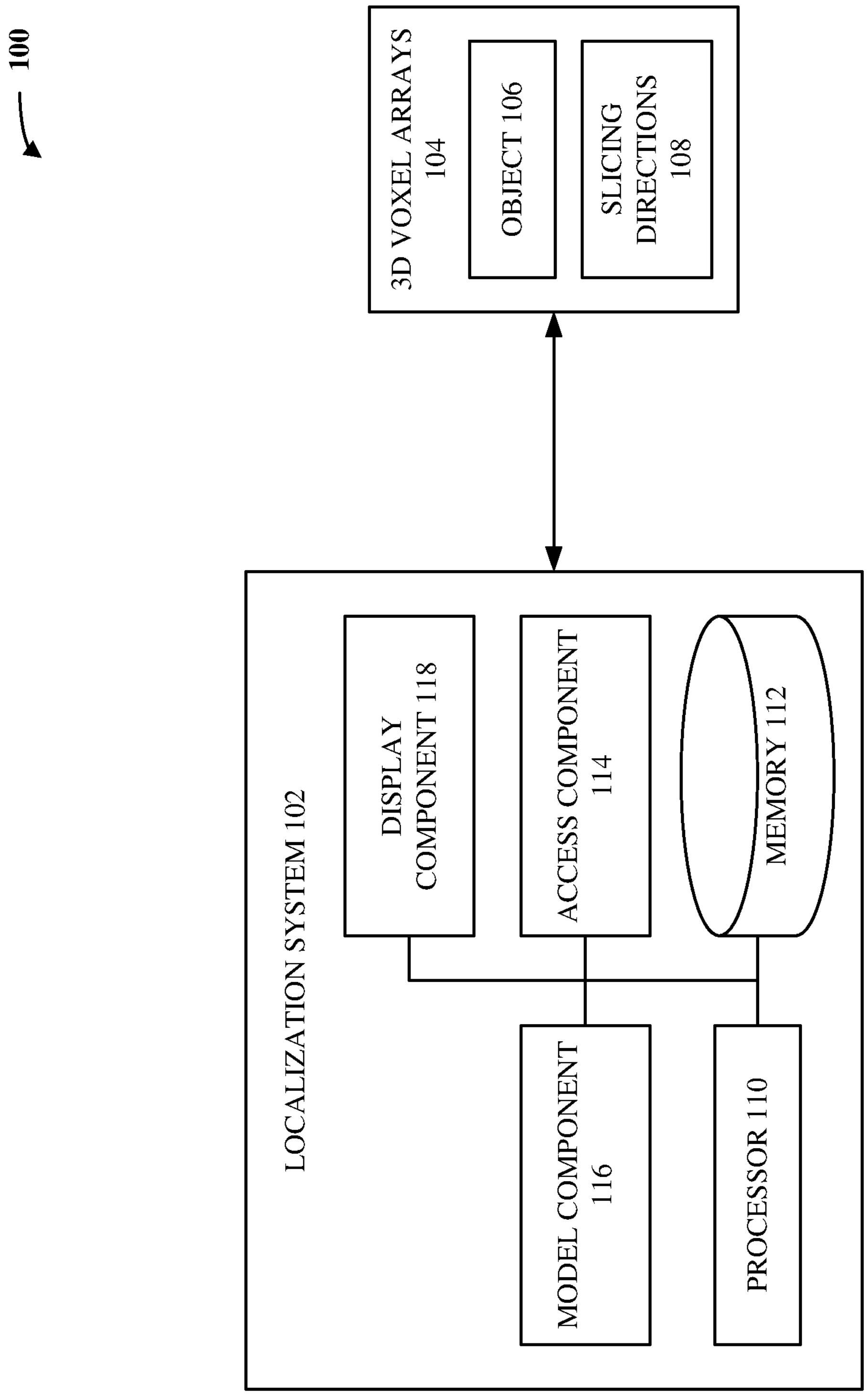
FIG. 1 illustrates a block diagram of an example, non-limiting system that facilitates hybrid 3D-to-2D slice-wise object localization ensembles in accordance with one or more embodiments described herein.

The following detailed description is merely illustrative and is not intended to limit embodiments or application/uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

A three-dimensional voxel array (e.g., which can be captured or generated by a computed tomography (CT) scanner, a magnetic resonance imaging (MRI) scanner, an X-ray scanner, an ultrasound scanner, or a positron emission tomography (PET) scanner) can depict an object (e.g., an anatomical structure of a medical patient, or an injury, malignancy, or irregularity of such anatomical structure). A deep learning neural network can be trained (e.g., in supervised fashion, unsupervised fashion, or reinforcement learning fashion) to localize that object (e.g., to identify where within the voxel array the object is located). Existing techniques either: cause the deep learning neural network to achieve a high localization accuracy at the expense of excessive consumption of computational resources; or cause the deep learning neural network to consume fewer computational resources at the expense of deteriorated inferencing accuracy.

In particular, when some existing techniques are implemented, the deep learning neural network is configured to operate in a wholly three-dimensional fashion. That is, the deep learning neural network is configured to receive as input the entire three-dimensional voxel array and to produce as output a three-dimensional object location indicator (e.g., a voxel-wise segmentation mask or a three-dimensional bounding box) that specifies where the object is positioned within the three-dimensional voxel array. For purposes of the herein disclosure, such existing techniques can be referred to as 3D-only techniques. Unfortunately, 3D-only techniques consume excessive computational resources (e.g., the deep learning neural network can have too many internal parameters, can take up too much memory storage space, or otherwise can consume too much time during inference or training).

When other existing techniques are implemented, the deep learning neural network is instead configured to operate in a wholly two-dimensional fashion. That is, the deep learning neural network is configured to receive as input not the three-dimensional voxel array in its entirety, but instead only an individual slice of the three-dimensional voxel array, and the deep learning neural network is configured to produce as output a two-dimensional object location indicator (e.g., a pixel-wise segmentation mask or a two-dimensional bounding box) that specifies where the object (or a portion thereof) is positioned within that slice. For purposes of the herein disclosure, such existing techniques can be referred to as 2D-only techniques. Such 2D-only techniques do not consume excessive computational resources (e.g., the deep learning neural network can have significantly fewer internal parameters, can take up much less memory storage space, or can otherwise consume much less time during inference or training). However, 2D-only techniques regrettably exhibit significantly reduced localization accuracy (e.g., the outputted two-dimensional location indicators are more likely to be incorrect).

Accordingly, systems or techniques that can cause the deep learning neural network to consume fewer computational resources without suffering deterioration of localization accuracy can be desirable.

Various embodiments described herein can address one or more of these technical problems. One or more embodiments described herein can include systems, computer-implemented methods, apparatus, or computer program products that can facilitate hybrid 3D-to-2D slice-wise object localization ensembles. In other words, the inventors of various embodiments described herein devised various techniques that can enable the deep learning neural network to consume fewer computational resources without suffering a commensurate degradation in localization accuracy.

In particular, the present inventors realized that the inferencing accuracy of the deep learning neural network can significantly depend upon what dimensionality of input that the deep learning neural network is configured to receive, and the present inventors further realized that the computational footprint of the deep learning neural network can significantly depend upon what dimensionality of output that the deep learning neural network is configured to produce.

For example, as mentioned above, 3D-only techniques cause the deep learning neural network to receive as input the entire three-dimensional voxel array and to produce as output a three-dimensional object location indicator. As also mentioned above, 2D-only techniques cause the deep learning neural network to receive as input a two-dimensional slice of the three-dimensional voxel array and to produce as output a two-dimensional object location indicator corresponding to that slice. The present inventors realized that the heightened localization accuracy of 3D-only techniques is significantly attributable to the fact that they perform at least some processing on the three-dimensional voxel array in its entirety, and the present inventors conversely realized that the deteriorated localization accuracy of 2D-only techniques is significantly attributable to the fact that they process only a single slice of the three-dimensional voxel array in isolation and perform no processing on the three-dimensional voxel array in its entirety. After all, object localization can be considered as an inherently spatial inferencing task, and three-dimensional data (e.g., sequences of related or adjacent slices) can be considered as providing fuller, richer, or otherwise more complete spatial information as compared to two-dimensional data (e.g., a single slice in isolation). In other words, valuable interslice contextual information can be lost by only considering individual slices of the three-dimensional voxel array one at a time by themselves. Moreover, the present inventors realized that the smaller computational footprint of 2D-only techniques is significantly attributable to the fact that their outputs are two-dimensional, and the present inventors conversely realized that the excessively large computational footprint of 3D-only techniques is significantly attributable to the fact that their outputs are three-dimensional. Indeed, the present inventors found, through experimentation, that configuring the deep learning neural network to generate three-dimensional object location indicators added significant architectural complexity and led to training convergence difficulties, whereas configuring the deep learning neural network to instead generate two-dimensional object location indicators ameliorated such complexity and difficulties.

Accordingly, the present inventors devised various embodiments described herein, which can involve configuring the deep learning neural network to receive as input the entirety of the three-dimensional voxel array and to produce as output multiple slice-wise two-dimensional object location indicators (e.g., a respective 2D object location indicator per slice of the three-dimensional voxel array), rather than producing a three-dimensional object location indicator. In various cases, this can be referred to as a hybrid 3D-to-2D slice-wise configuration. Using such a hybrid slice-wise configuration, the deep learning neural network can achieve a reduced computational footprint (e.g., it can take fewer computational resources to compute two-dimensional object location indicators than to compute three-dimensional object location indicators) without experiencing a commensurate deterioration in localization accuracy (e.g., by receiving the entire three-dimensional voxel array as input, the deep learning neural network can make use of the valuable interslice contextual information that would otherwise be lost if the deep learning neural network instead received as input only an isolated slice of the three-dimensional voxel array).

Moreover, note that the multiple slice-wise two-dimensional object location indicators produced by various embodiments described herein can be considered as much less computationally expensive to produce than a three-dimensional object location indicator, while at the same time being just as informative as that three-dimensional object location indicator would be. Indeed, such multiple slice-wise two-dimensional object location indicators can be considered as collectively approximating some three-dimensional object location indicator. In other words, each of such multiple slice-wise two-dimensional object location indicators can be considered as being a respective cross-section or slice of that approximated three-dimensional object location indicator. In still other words, although each of such multiple slice-wise two-dimensional object location indicators can be considered as providing no out-of-plane localization information by itself, they can together be considered as collectively estimating or approximating such out-of-plane localization information, due to how such multiple slice-wise two-dimensional object location indicators are spatially interrelated to each other (e.g., if two slices of the three-dimensional voxel array are spatially adjacent to each other, then the two two-dimensional object location indicators that are respectively produced for those two slices can themselves be considered as being spatially adjacent to each other). In this way, predicting a respective two-dimensional object location indicator for each slice of an inputted three-dimensional voxel array can be considered as an inexpensive-but-equally-informative substitute for predicting a three-dimensional object location indicator for the inputted three-dimensional voxel array. In stark contrast, predicting only a single two-dimensional object location indicator for an inputted three-dimensional voxel array would be considered as an inexpensive-but-significantly-less-informative substitute for predicting a three-dimensional object location indicator.

Thus, various embodiments described herein can be considered as enabling the deep learning neural network to experience the best of both worlds: to exhibit a smaller computational footprint than 3D-only techniques, and to nevertheless exhibit a higher localization accuracy than 2D-only techniques.

Furthermore, the present inventors realized that localization accuracy can be improved even more by leveraging an ensemble of deep learning neural networks, each of which can exhibit a 3D-to-2D configuration, and each of which can be trained to operate on three-dimensional voxel arrays captured or generated according to a respective slicing direction. Accordingly, if multiple three-dimensional voxel arrays are available, each depicting the object that is to be localized and each captured or generated according to a respective slicing direction, such multiple three-dimensional voxel arrays can be respectively processed by the deep learning neural networks of the ensemble. By considering all of such multiple three-dimensional voxel arrays, the likelihood of accurately localizing the object can be increased, since different slicing directions can result in different in-plane resolutions, and since the object might be more easily localized in one plane (e.g., axial plane) than another (e.g., sagittal plane).

Various embodiments described herein can be considered as a computerized tool (e.g., any suitable combination of computer-executable hardware or computer-executable software) that can facilitate hybrid 3D-to-2D slice-wise object localization ensembles. In various aspects, such computerized tool can comprise an access component, a model component, or a display component.

In various embodiments, there can be a set of three-dimensional voxel arrays. In various aspects, each of the set of three-dimensional voxel arrays can comprise any suitable number or arrangement of voxels. In various instances, the set of three-dimensional voxel arrays can have been captured by any suitable imaging equipment in any suitable operational context (e.g., can have been captured in a medical/clinical operational context by medical imaging equipment, such as X-ray scanners, MRI scanners, PET scanners, CT scanners, or ultrasound scanners). In any case, the set of three-dimensional voxel arrays can each depict a same object as each other. However, each of the set of three-dimensional voxel arrays can have been generated or captured according to a distinct or respective slicing direction. Accordingly, each of the set of three-dimensional voxel arrays can be considered as illustrating or depicting the object via a distinct or respective in-plane resolution or out-of-plane resolution.

As a non-limiting example, the set of three-dimensional voxel arrays can comprise three voxel arrays that each depict the object: a first voxel array that was captured or generated via an axial slicing direction, a second voxel array that was captured or generated via a coronal slicing direction, and a third voxel array that was captured or generated via a sagittal slicing direction. Although each of such three voxel arrays can be considered as depicting or illustrating the object, their different slicing directions can cause them to depict or illustrate the object via distinct, direction-dependent spatial resolutions.

In particular, because the first voxel array can have been captured or generated according to an axial slicing direction, the first voxel array can be considered as a sequence of axial slices, where each axial slice can be considered as a two-dimensional plane that is orthogonal to the axial slicing direction. Thus, the first voxel array can be considered as having a higher or better spatial resolution (e.g., as depicting or illustrating visual details more clearly) along directions that are orthogonal to the axial slicing direction (e.g., if the axial slicing direction runs top-to-bottom, then the first voxel array can have better resolution in planes that are spanned by front-to-back and right-to-left directions).

Similarly, because the second voxel array can have been captured or generated according to a coronal slicing direction, the second voxel array can be considered as a sequence of coronal slices, where each coronal slice can be considered as a two-dimensional plane that is orthogonal to the coronal slicing direction. So, the second voxel array can be considered as having a higher or better spatial resolution along directions that are orthogonal to the coronal slicing direction (e.g., if the coronal slicing direction runs front-to-back, then the second voxel array can have better resolution in planes that are spanned by right-to-left and top-to-bottom directions).

Likewise, because the third voxel array can have been captured or generated according to a sagittal slicing direction, the third voxel array can be considered as a sequence of sagittal slices, where each sagittal slice can be considered as a two-dimensional plane that is orthogonal to the sagittal slicing direction. Accordingly, the third voxel array can be considered as having a higher or better spatial resolution along directions that are orthogonal to the sagittal slicing direction (e.g., if the sagittal slicing direction runs right-to-left, then the third voxel array can have better resolution in planes that are spanned by front-to-back and top-to-bottom directions).

Accordingly, even though each of these three voxel arrays can depict or illustrate the same object as each other, it can be possible that the object or portions thereof are more easily seen in one of these voxel arrays than in others. For instance, suppose that the object is oriented primarily along the axial slicing direction. In such case, the object might be more easily seen in the second and third voxel arrays than in the first voxel array. As another instance, suppose that the object is oriented primarily along the coronal slicing direction. In such case, the object might be more easily seen in the first and third voxel arrays than in the second voxel array. As yet another instance, suppose that the object is oriented primarily along the sagittal slicing direction. In such case, the object might be more easily seen in the first and second voxel arrays than in the third voxel array.

In any case, it can be desired to localize the object in the set of three-dimensional voxel arrays. As described herein, the computerized tool can facilitate such localization.

In various embodiments, the access component of the computerized tool can electronically receive or otherwise electronically access the set of three-dimensional voxel arrays. In some aspects, the access component can electronically retrieve the set of three-dimensional voxel arrays from any suitable centralized or decentralized data structures (e.g., graph data structures, relational data structures, hybrid data structures), whether remote from or local to the access component. In any case, the access component can electronically obtain or access the set of three-dimensional voxel arrays, such that other components of the computerized tool can electronically interact with (e.g., read, write, edit, copy, manipulate) the set of three-dimensional voxel arrays.

In various embodiments, the model component of the computerized tool can electronically store, maintain, control, or otherwise access a deep learning ensemble. In various aspects, the model component can electronically execute the deep learning ensemble on the set of three-dimensional voxel arrays, thereby yielding various two-dimensional object location indicators and various confidence scores respectively corresponding to the two-dimensional object location indicators.

More specifically, for each given slicing direction represented by the set of three-dimensional voxel arrays, the deep learning ensemble can include a respective deep learning neural network that is configured to operate on data captured or generated according to that given slicing direction.

As a non-limiting example, since the set of three-dimensional voxel arrays can include a first voxel array captured or generated via an axial slicing direction, the deep learning ensemble can include a first deep learning neural network that is configured to operate on axially-captured data. As another non-limiting example, since the set of three-dimensional voxel arrays can include a second voxel array captured or generated via a coronal slicing direction, the deep learning ensemble can include a second deep learning neural network that is configured to operate on coronally-captured data. As even another non-limiting example, since the set of three-dimensional voxel arrays can include a third voxel array captured or generated via a sagittal slicing direction, the deep learning ensemble can include a third deep learning neural network that is configured to operate on sagittally-captured data.

In various aspects, any deep learning neural network in the deep learning ensemble can exhibit any suitable internal architecture. For example, any deep learning neural network in the deep learning ensemble can include any suitable numbers of any suitable types of layers (e.g., input layer, one or more hidden layers, output layer, any of which can be convolutional layers, dense layers, non-linearity layers, pooling layers, batch normalization layers, or padding layers). As another example, any deep learning neural network in the deep learning ensemble can include any suitable numbers of neurons in various layers (e.g., different layers can have the same or different numbers of neurons as each other). As yet another example, any deep learning neural network in the deep learning ensemble can include any suitable activation functions (e.g., softmax, sigmoid, hyperbolic tangent, rectified linear unit) in various neurons (e.g., different neurons can have the same or different activation functions as each other). As still another example, any deep learning neural network in the deep learning ensemble can include any suitable interneuron connections or interlayer connections (e.g., forward connections, skip connections, recurrent connections).

In any case, each deep learning neural network in the deep learning ensemble can be configured to perform object localization on inputted voxel arrays. However, rather than being configured to generate three-dimensional object location indicators, each of such deep learning neural networks can instead be configured to generate slice-wise two-dimensional object location indicators. That is, each deep learning neural network of the deep learning ensemble can be configured in a hybrid 3D-to-2D slice-wise fashion.

Accordingly, the model component can, in various aspects, execute respective ones of the deep learning ensemble on respective ones of the set of three-dimensional voxel arrays, thereby yielding respective ones of the various two-dimensional object location indicators and the various confidence scores.

As a non-limiting example, the model component can execute the first deep learning neural network on the first voxel array, and such execution can yield a set of first two-dimensional object location indicators and a set of first confidence scores. More specifically, as mentioned above, the first voxel array can be considered as a sequence of axial slices. In various aspects, the model component can feed the first voxel array (e.g., that sequence of axial slices) to an input layer of the first deep learning neural network, the first voxel array (e.g., that sequence of axial slices) can complete a forward pass through one or more hidden layers of the first deep learning neural network, and an output layer of the first deep learning neural network can compute the set of first two-dimensional object location indicators and the set of first confidence scores, based on activations from the one or more hidden layers of the first deep learning neural network.

In various aspects, the set of first two-dimensional object location indicators can respectively correspond to the sequence of axial slices of the first voxel array. That is, the first deep learning neural network can produce a respective two-dimensional object location indicator for each axial slice of the first voxel array. In various instances, each of the set of first two-dimensional object location indicators can be a predicted or inferred pixel-wise segmentation mask or two-dimensional bounding box that indicates or otherwise conveys where the object (or a portion thereof) is specifically located or positioned within a respective axial slice of the first voxel array. In various cases, the set of first confidence scores can respectively correspond to the set of first two-dimensional object location indicators. That is, the first deep learning neural network can produce not only a respective two-dimensional object location indicator for each given axial slice of the first voxel array, but can also produce a respective confidence score which can be a scalar indicating how much or how little confidence or certainty is associated with that respective two-dimensional object location indicator.

As another non-limiting example, the model component can execute the second deep learning neural network on the second voxel array, and such execution can yield a set of second two-dimensional object location indicators and a set of second confidence scores. More specifically, as mentioned above, the second voxel array can be considered as a sequence of coronal slices. In various aspects, the model component can feed the second voxel array (e.g., that sequence of coronal slices) to an input layer of the second deep learning neural network, the second voxel array (e.g., that sequence of coronal slices) can complete a forward pass through one or more hidden layers of the second deep learning neural network, and an output layer of the second deep learning neural network can compute the set of second two-dimensional object location indicators and the set of second confidence scores, based on activations from the one or more hidden layers of the second deep learning neural network.

In various instances, the set of second two-dimensional object location indicators can respectively correspond to the sequence of coronal slices of the second voxel array. That is, the second deep learning neural network can produce a respective two-dimensional object location indicator for each coronal slice of the second voxel array. In various cases, each of the set of second two-dimensional object location indicators can be a predicted or inferred pixel-wise segmentation mask or two-dimensional bounding box that indicates or otherwise conveys where the object (or a portion thereof) is specifically located or positioned within a respective coronal slice of the second voxel array. In various aspects, the set of second confidence scores can respectively correspond to the set of second two-dimensional object location indicators. That is, the second deep learning neural network can produce not only a respective two-dimensional object location indicator for each given coronal slice of the second voxel array, but can also produce a respective confidence score which can be a scalar indicating how much or how little confidence or certainty is associated with that respective two-dimensional object location indicator.

As yet another non-limiting example, the model component can execute the third deep learning neural network on the third voxel array, and such execution can yield a set of third two-dimensional object location indicators and a set of third confidence scores. More specifically, as mentioned above, the third voxel array can be considered as a sequence of sagittal slices. In various aspects, the model component can feed the third voxel array (e.g., that sequence of sagittal slices) to an input layer of the third deep learning neural network, the third voxel array (e.g., that sequence of sagittal slices) can complete a forward pass through one or more hidden layers of the third deep learning neural network, and an output layer of the third deep learning neural network can compute the set of third two-dimensional object location indicators and the set of third confidence scores, based on activations from the one or more hidden layers of the third deep learning neural network.

In various instances, the set of third two-dimensional object location indicators can respectively correspond to the sequence of sagittal slices of the third voxel array. That is, the third deep learning neural network can produce a respective two-dimensional object location indicator for each sagittal slice of the third voxel array. In various cases, each of the set of third two-dimensional object location indicators can be a predicted or inferred pixel-wise segmentation mask or two-dimensional bounding box that indicates or otherwise conveys where the object (or a portion thereof) is specifically located or positioned within a respective sagittal slice of the third voxel array. Just as above, the set of third confidence scores can respectively correspond to the set of third two-dimensional object location indicators. That is, the third deep learning neural network can produce not only a respective two-dimensional object location indicator for each given sagittal slice of the third voxel array, but can also produce a respective confidence score which can be a scalar indicating how much or how little confidence or certainty is associated with that respective two-dimensional object location indicator.

In various instances, note that it can be possible for the set of three-dimensional voxel arrays to include fewer than three voxel arrays. In such case, the model component can execute fewer than all of the deep learning neural networks in the deep learning ensemble, and the remaining deep learning neural networks in the deep learning ensemble can sit idle. As a non-limiting example, suppose that the set of three-dimensional voxel arrays comprises only the first voxel array and not the second or third voxel arrays. In such case, the model component can execute the first deep learning neural network on the first voxel array, and the second and third deep learning neural networks can be inactive or idle during such execution. Accordingly, object localization can be performed, even if only one or two three-dimensional voxel arrays are available (e.g., even if not all of the slicing directions have been utilized).

In any case, and as mentioned above, because each deep learning neural network of the deep learning ensemble can receive as input a three-dimensional voxel array and can produce as output a respective two-dimensional object location indicator for each slice of that three-dimensional voxel array, each deep learning neural network of the deep learning ensemble can be considered as exhibiting a hybrid 3D-to-2D slice-wise configuration. In various aspects, such hybrid 3D-to-2D slice-wise configuration can be accomplished by any suitable internal architecture whose upstream layers are operable on three-dimensional data (e.g., such upstream layers can include three-dimensional convolutional layers), whose downstream layers are operable on two-dimensional data (e.g., such downstream layers can include two-dimensional convolutional layers), and whose resampling or resizing layers (e.g., upsampling layers, downsampling layers) do not perform resampling or resizing along whatever slicing direction is at issue. In such case, the upstream layers can receive as input a respective three-dimensional voxel array and can produce as output various three-dimensional hidden activation maps (e.g., the results obtained via three-dimensional convolutions). Note that each of such three-dimensional hidden activation maps can have the same number of slices as the inputted three-dimensional voxel array, due to the above-mentioned restriction of resampling or resizing operations. In various instances, for any given slice index (e.g., for a j-th slice of the inputted three-dimensional voxel array, for any suitable positive integer j), the downstream layers can receive as input whichever individual slices of those three-dimensional hidden activation maps are located at that given slice index (e.g., the j-th slice of each of those three-dimensional hidden activation maps) and can produce as output a two-dimensional object location indicator and confidence score. Such two-dimensional object location indicator and confidence score can be considered as corresponding to whichever slice of the inputted three-dimensional voxel array corresponds to that given slice index (e.g., can be considered as corresponding to the j-th slice of the inputted three-dimensional voxel array). In various cases, the downstream layers can be repeatedly executed in parallel (e.g., via weight sharing) for all available slice indices (e.g., for all available j), so as to collectively yield a respective two-dimensional object location indicator and confidence score for each slice index, and thus for each slice of the inputted three-dimensional voxel array.

As a non-limiting example, each deep learning neural network of the deep learning ensemble can exhibit a modified RetinaNet architecture. Recall that a traditional RetinaNet architecture can include a ResNet backbone, a Feature Pyramid Network (FPN) that is downstream of the ResNet backbone, and confidence and bounding box subnetworks that are downstream of the FPN. In the modified RetinaNet architecture, all two-dimensional convolutional kernels in the ResNet backbone can be replaced with three-dimensional convolutional kernels. For instance, such two-dimensional convolutional kernels can be converted to three dimensions via 3D axial-sagittal-coronal (ACS) kernel conversion techniques. In contrast, the two-dimensional convolutional kernels of the FPN can be maintained or preserved (e.g., can be not replaced with three-dimensional convolutional kernels). Furthermore, in the modified RetinaNet architecture, all downsampling (or upsampling) operations can be set to not downsample (or upsample) along whatever slicing direction is at issue (e.g., the slicing direction of the first deep learning neural network can be the axial slicing direction; the slicing direction of the second deep learning neural network can be the coronal slicing direction; the slicing direction of the third deep learning neural network can be the sagittal slicing direction). Accordingly, all hidden activations internally computed throughout the modified RetinaNet architecture can comprise the same number of slices as whatever voxel array is received as input. Further still, in the modified RetinaNet architecture, the FPN and the confidence and bounding box subnetworks can be applied, via weight sharing, on a slice-wise basis (e.g., can be applied to each slice individually), due to the absence of downsampling along the slicing direction. Accordingly, such a modified RetinaNet architecture can receive a three-dimensional voxel array as input and produce as output a respective two-dimensional bounding box and confidence score for each slice of that inputted three-dimensional voxel array.

In any case, the model component can execute the deep learning ensemble on the set of three-dimensional voxel arrays, and the result of such execution can be the various two-dimensional object location indicators and corresponding confidence scores.

In various embodiments, the display component of the computerized tool can take any suitable electronic actions based on the various confidence scores. As a non-limiting example, if none of the various confidence scores satisfy any suitable threshold, then the display component can electronically render, on any suitable electronic display, an electronic notification indicating that the object has not been detected within the set of three-dimensional voxel arrays. As another non-limiting example, if any given confidence score satisfies the threshold, then the display component can electronically render, on the electronic display, an electronic notification indicating that the object has been detected within the set of three-dimensional voxel arrays. As yet another non-limiting example, if any given confidence score satisfies the threshold, then the display component can electronically render, on the electronic display, whichever two-dimensional object location indicator corresponds to that given confidence score. In various instances, the above-mentioned threshold can be a user-defined variable. That is, a user of the computerized tool can select or choose the value or magnitude of the threshold, via any suitable human-computer interface device (e.g., keyboard, keypad, touchscreen, voice command).

In order to help ensure that the two-dimensional object location indicators and confidence scores generated by the deep learning ensemble are accurate, each of the deep learning neural networks of the deep learning ensemble can be trained via any suitable training paradigm. For instance, the computerized tool can comprise a training component that can train each of the deep learning neural networks of the deep learning ensemble on a training dataset. As a non-limiting example, the training dataset can be annotated, and the training component can thus facilitate supervised training of each of the deep learning neural networks in the deep learning ensemble.

Various embodiments described herein can be employed to use hardware or software to solve problems that are highly technical in nature (e.g., to facilitate hybrid 3D-to-2D slice-wise object localization ensemble), that are not abstract and that cannot be performed as a set of mental acts by a human. Further, some of the processes performed can be performed by a specialized computer (e.g., deep learning neural networks having internal parameters such as convolutional kernels) for carrying out defined acts related to object localization.

Such defined acts can include: accessing, by a device operatively coupled to a processor, at least one three-dimensional voxel array; and localizing, by the device and via execution of a deep learning ensemble, an object depicted in the at least one three-dimensional voxel array, wherein the deep learning ensemble receives as input the at least one three-dimensional voxel array, and wherein the deep learning ensemble produces as output a set of two-dimensional object location indicators respectively corresponding to a set of two-dimensional slices of the at least one three-dimensional voxel array. In various instances, the deep learning ensemble can comprise a first deep learning neural network, a second deep learning neural network, and a third deep learning neural network that are in parallel with each other; the at least one three-dimensional voxel array can comprise a first three-dimensional voxel array made up of axial two-dimensional slices, a second three-dimensional voxel array made up of coronal two-dimensional slices, and a third three-dimensional voxel array made up of sagittal two-dimensional slices; the first deep learning neural network can receive as input the first three-dimensional voxel array and can produce as output, for each of the axial two-dimensional slices of the first three-dimensional voxel array, a respective one of the set of two-dimensional object location indicators; the second deep learning neural network can receive as input the second three-dimensional voxel array and can produce as output, for each of the coronal two-dimensional slices of the second three-dimensional voxel array, a respective one of the set of two-dimensional object location indicators; and the third deep learning neural network can receive as input the third three-dimensional voxel array and can produce as output, for each of the sagittal two-dimensional slices of the third three-dimensional voxel array, a respective one of the set of two-dimensional object location indicators.

Such defined acts are not performed manually by humans. Indeed, neither the human mind nor a human with pen and paper can perform object localization by executing deep learning neural networks on axially-captured, coronally-captured, or sagittally-captured voxel arrays. Indeed, a deep learning neural network is an inherently-computerized construct that simply cannot be meaningfully executed or trained in any way by the human mind without computers. Furthermore, object localization is an inherently-computerized inferencing task focused on equipping computers with the ability to localize objects depicted in electronic images. Thus, object localization as described herein cannot be meaningfully implemented in any way by the human mind without computers. Accordingly, a computerized tool that can localize objects depicted in three-dimensional voxel arrays, via execution of deep learning neural networks, is likewise inherently-computerized and cannot be implemented in any sensible, practical, or reasonable way without computers.

Moreover, various embodiments described herein can integrate into a practical application various teachings relating to hybrid 3D-to-2D slice-wise object localization ensembles. As explained above, 3D-only object localization techniques achieve good localization accuracy at the expensive of excessive consumption of computational resources, whereas 2D-only object localization techniques consume fewer computational resources at the expense of deteriorated localization accuracy. The present inventors realized that the accuracy boost of 3D-only object localization techniques can be significantly attributed to the fact that they perform at least some amount of processing on an entirety of a given three-dimensional voxel array. In this way, 3D-only object localization techniques are able to leverage rich interslice contextual information that is present in the given three-dimensional voxel array. In contrast, 2D-only object localization techniques do not perform any amount of processing on the entirety of the given three-dimensional voxel array and thus cannot make use of that rich interslice contextual information, thereby causing them to exhibit degraded localization accuracy. Furthermore, the present inventors realized that the smaller computational footprint of 2D-only object localization techniques can be significantly attributed to the fact that they generate two-dimensional outputs (e.g., pixel-wise segmentation masks, two-dimensional bounding boxes). In contrast, 3D-only object localization techniques generate three-dimensional outputs (e.g., voxel-wise segmentation masks, three-dimensional bounding boxes), which can introduce significant architecture complexity and training difficulties.

Accordingly, the present inventors devised various embodiments described herein to address such technical problems. In particular, various embodiments described herein can involve configuring a deep learning neural network to receive as input a three-dimensional voxel array but to produce two-dimensional outputs instead of three-dimensional outputs. In particular, the deep learning neural network as described herein can produce a respective two-dimensional location indicator (e.g., pixel-wise segmentation mask, two-dimensional bounding box) per slice of the three-dimensional voxel array. As mentioned above, this can be referred to as a hybrid 3D-to-2D slice-wise localization configuration. With such configuration, the deep learning neural network can perform at least some processing on the entirety of the three-dimensional voxel array, thereby obtaining an accuracy boost analogous to 3D-only object localization techniques, while simultaneously exhibiting reduced architecture complexity and training difficulties, analogous to 2D-only object localization techniques.

Furthermore, even though the slice-wise two-dimensional location indicators can be much less expensive to generate than a three-dimensional location indicator would be, the slice-wise two-dimensional location indicators can nevertheless be just as informative or useful as that three-dimensional location indicator would be. Indeed, as mentioned above, the slice-wise two-dimensional location indicators can be considered as collectively approximating that three-dimensional location indicator. That is, if the slice-wise two-dimensional location indicators were physically or spatially stacked on top of each other, such stack would be considered as a close approximation or estimation of that three-dimensional location indicator. In other words, a single two-dimensional location indicator can provide no out-of-plane localization information by itself, but a plurality of two-dimensional location indicators representing respective slices can be considered as collectively approximating such out-of-plane localization information. Accordingly, producing a respective two-dimensional location indicator per slice of the three-dimensional voxel array can be considered as a more efficient, yet not less informative, alternative to producing a three-dimensional location indicator for the three-dimensional voxel array.

Therefore, various embodiments described herein can be considered as enabling the deep learning neural network to experience the best of both worlds: higher localization accuracy than 2D-only techniques, with a smaller computational footprint than 3D-only techniques.

Additionally, the present inventors realized that localization accuracy can be improved even further by utilizing an ensemble of deep learning neural networks, each of which can exhibit a hybrid 3D-to-2D slice-wise localization configuration, and each of which can be trained to process voxel arrays that have been generated or captured according to a distinct or unique slicing direction. For example, such ensemble can include a first deep learning neural network that can be trained to process axially-captured voxel arrays, a second deep learning neural network that can be trained to process coronally-captured voxel arrays, and a third deep learning neural network that can be trained to process sagittally-captured voxel arrays. Accordingly, if multiple voxel arrays depicting the object are available, each having been captured according to a different slicing direction (e.g., an axially-captured voxel array, a coronally-captured voxel array, a sagittally-captured voxel array), such multiple voxel arrays can be processed in parallel by respective deep learning neural networks in the ensemble. The present inventors realized that this can boost localization accuracy, since voxel arrays that are captured or generated according to different slicing directions can exhibit different in-plane resolutions. In particular, depending upon the orientation of the object that is desired to be localized, that object might be more easily viewable, and thus more easily or accurately localizable, in a voxel array that is captured or generated according to a particular slicing direction (e.g., axial slicing direction) than a different slicing direction (e.g., sagittal slicing direction). Thus, by processing in parallel multiple voxel arrays that depict the same object as each other but according to different slicing directions, the likelihood of accurately localizing the object can be increased.

For at least these reasons, various embodiments described herein facilitate concrete and tangible technical improvements in the field of object localization, and such embodiments thus clearly qualify as useful and practical applications of computers.

Furthermore, various embodiments described herein can control real-world tangible devices based on the disclosed teachings. For example, various embodiments described herein can electronically train or execute real-world deep learning neural networks on real-world voxel arrays (e.g., created by real-world X-ray scanners or CT scanners), and can electronically render real-world localization results (e.g., pixel-wise segmentation masks, two-dimensional bounding boxes) on real-world computer screens.

It should be appreciated that the herein figures and description provide non-limiting examples of various embodiments and are not necessarily drawn to scale.

FIG. 1 illustrates a block diagram of an example, non-limiting system 100 that can facilitate hybrid 3D-to-2D slice-wise object localization ensembles in accordance with one or more embodiments described herein. As shown, a localization system 102 can be electronically integrated, via any suitable wired or wireless electronic connections, with a set of 3D voxel arrays 104.

In various embodiments, the set of 3D voxel arrays 104 can comprise any suitable number of three-dimensional voxel arrays, each of which can comprise any suitable number or arrangement of voxels. In various aspects, the set of 3D voxel arrays 104 can have been captured or otherwise generated by any suitable imaging equipment. As a non-limiting example, the set of 3D voxel arrays 104 can have been captured or generated by a CT scanner (not shown), in which case each of the set of 3D voxel arrays 104 can be considered as a three-dimensional CT scanned image. As another non-limiting example, the set of 3D voxel arrays 104 can have been captured or generated by an X-ray scanner (not shown), in which case each of the set of 3D voxel arrays 104 can be considered as a three-dimensional X-ray scanned image. As yet another non-limiting example, the set of 3D voxel arrays 104 can have been captured or generated by an MRI scanner (not shown), in which case each of the set of 3D voxel arrays 104 can be considered as a three-dimensional MRI scanned image. As even another non-limiting example, the set of 3D voxel arrays 104 can have been captured or generated by an ultrasound scanner (not shown), in which case each of the set of 3D voxel arrays 104 can be considered as a three-dimensional ultrasound scanned image. As still another non-limiting example, the set of 3D voxel arrays 104 can have been captured or generated by a PET scanner (not shown), in which case each of the set of 3D voxel arrays 104 can be considered as a three-dimensional PET scanned image.

In any case, each of the set of 3D voxel arrays 104 can visually illustrate or depict an object 106. In various aspects, the object 106 can be any suitable visually-perceptible thing which can depend upon an operational context of the localization system 102. As a non-limiting example, suppose that the localization system 102 is implemented in a medical or clinical operational context. In such case, the object 106 can be any suitable anatomical structure (e.g., body part, organ, tissue, bodily fluid), any suitable portion of the anatomical structure, or any suitable injury or pathology associated with the anatomical structure. For instance, the object 106 can be a cervical spine of a medical patient, or the object 106 can be a fracture (e.g., a non-contrast, non-compressive fracture) within the cervical spine of the medical patient.

In various aspects, the set of 3D voxel arrays 104 can be considered as respectively corresponding (e.g., in one-to-one fashion) to a set of slicing directions 108. In various instances, each of the set of slicing directions 108 can be a unique or distinct linear direction or axis in three-space. In various cases, each of the set of 3D voxel arrays 104 can have been captured or generated according to a respective one of the set of slicing directions 108. In other words, each of the set of 3D voxel arrays 104 can be considered as being a sequence of two-dimensional slices, where such two-dimensional slices are orthogonal to and ordered along a respective one of the set of slicing directions 108. Because in-plane and out-of-plane spatial resolutions (e.g., visual clarity) of voxel arrays can depend upon slicing direction, each of the set of 3D voxel arrays 104 can be considered as visually depicting the object 106 according to a unique or distinct in-plane and out-of-plane spatial resolution. Non-limiting aspects are described with respect to FIG. 2.

Figure 2:
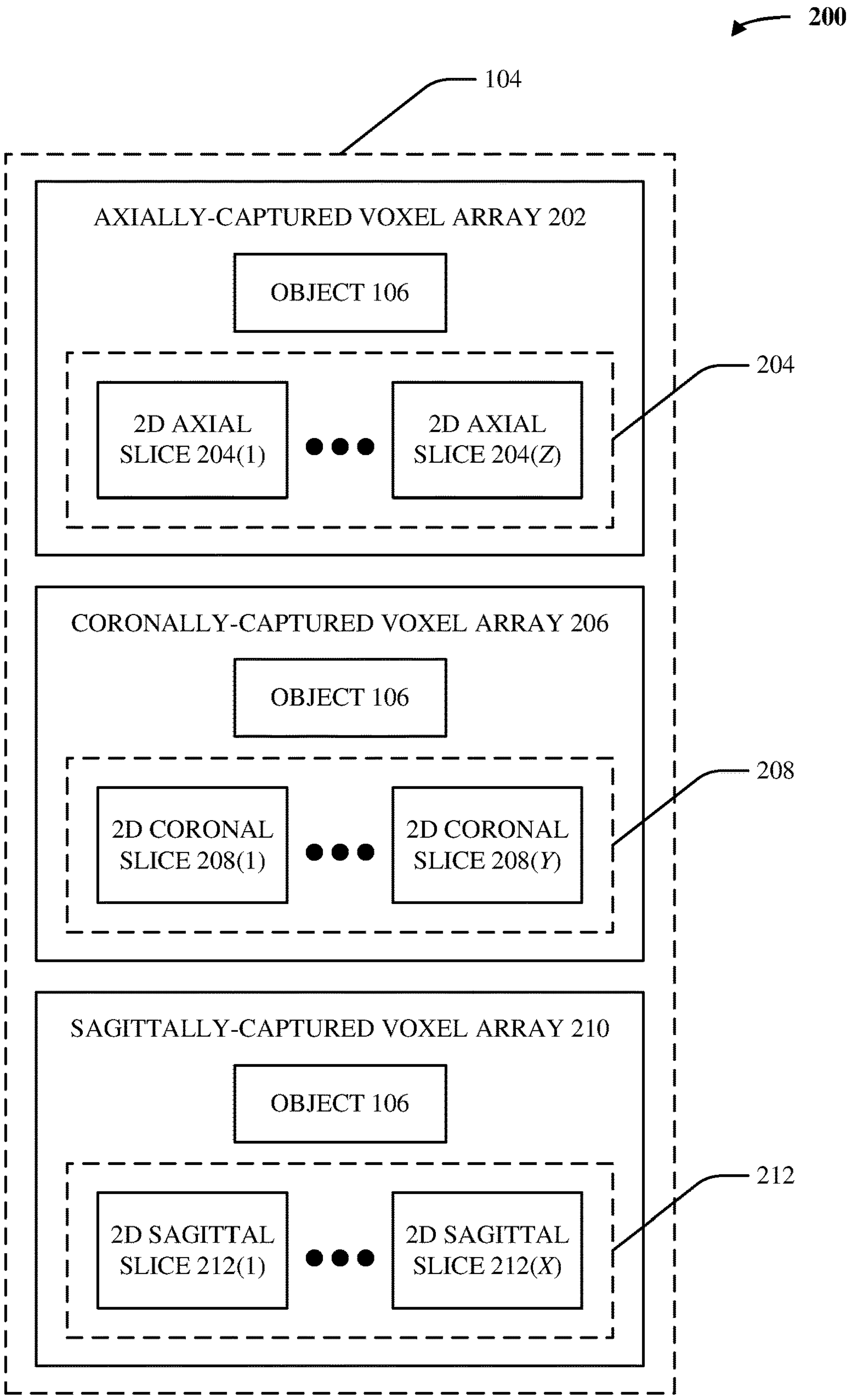
FIG. 2 illustrates an example, non-limiting block diagram of a set of three-dimensional voxel arrays in accordance with one or more embodiments described herein.

FIG. 2 illustrates an example, non-limiting block diagram 200 of the set of 3D voxel arrays 104 in accordance with one or more embodiments described herein.

In various aspects, the set of slicing directions 108 can comprise three mutually orthogonal directions in three-space: an axial slicing direction which can extend along a top-to-bottom axis; a coronal slicing direction which can extend along a front-to-back axis; and a sagittal slicing direction which can extend along a right-to-left axis. In such case, the set of 3D voxel arrays 104 can comprise three voxel arrays: an axially-captured voxel array 202; a coronally-captured voxel array 206; and a sagittally-captured voxel array 210.

In various instances, the axially-captured voxel array 202 can depict the object 106 and can comprise any suitable number or arrangement of voxels. As a non-limiting example, the axially-captured voxel array 202 can be an x-by-y-by-z voxel array, for any suitable positive integers x, y, and z. Without loss of generality, suppose that x can be considered as the number of voxels extending along the right-to-left axis, that y can be considered as the number of voxels extending along the front-to-back axis, and that z can be considered as the number of voxels extending along the top-to-bottom axis.

In various cases, the axially-captured voxel array 202 can, as its name suggests, have been captured or generated according to the axial slicing direction of the set of slicing directions 108. Thus, the axially-captured voxel array 202 can be considered as being made up of a set of 2D axial slices 204, where each of the set of 2D axial slices 204 can be a two-dimensional pixel array that is orthogonal to the axial slicing direction. Since the axial slicing direction can extend along a top-to-bottom axis, each of the set of 2D axial slices 204 can be an x-by-y slice of the axially-captured voxel array 202, and there can be a total of z of such slices: a 2D axial slice 204(1) to a 2D axial slice 204($z$).

Note that, because the axially-captured voxel array 202 can have been captured or generated according to the axial slicing direction, the axially-captured voxel array 202 can exhibit better spatial resolution, clarity, or detail in directions that are orthogonal to the axial slicing direction. Accordingly, if the object 106 is primarily or chiefly oriented along the axial slicing direction, the object 106 can be poorly visually perceptible in the axially-captured voxel array 202. On the other hand, if the object 106 is primarily or chiefly oriented along the coronal or sagittal slicing directions, the object 106 can be well visually perceptible in the axially-captured voxel array 202.

In various aspects, the coronally-captured voxel array 206 can depict the object 106 and can exhibit the same number or arrangement of voxels as the axially-captured voxel array 202. That is, the coronally-captured voxel array 206 can be an x-by-y-by-z voxel array.

In various instances, the coronally-captured voxel array 206 can, as its name suggests, have been captured or generated according to the coronal slicing direction of the set of slicing directions 108. So, the coronally-captured voxel array 206 can be considered as being made up of a set of 2D coronal slices 208, where each of the set of 2D coronal slices 208 can be a two-dimensional pixel array that is orthogonal to the coronal slicing direction. Since the coronal slicing direction can extend along a front-to-back axis, each of the set of 2D coronal slices 208 can be an x-by-z slice of the coronally-captured voxel array 206, and there can be a total of y of such slices: a 2D coronal slice 208(1) to a 2D coronal slice 208($y$).

Note that, because the coronally-captured voxel array 206 can have been captured or generated according to the coronal slicing direction, the coronally-captured voxel array 206 can exhibit better spatial resolution, clarity, or detail in directions that are orthogonal to the coronal slicing direction. Accordingly, if the object 106 is primarily or chiefly oriented along the coronal slicing direction, the object 106 can be poorly visually perceptible in the coronally-captured voxel array 206. On the other hand, if the object 106 is primarily or chiefly oriented along the axial or sagittal slicing directions, the object 106 can be well visually perceptible in the coronally-captured voxel array 206.

In various aspects, the sagittally-captured voxel array 210 can depict the object 106 and can exhibit the same number or arrangement of voxels as the axially-captured voxel array 202 and as the coronally-captured voxel array 206. That is, the sagittally-captured voxel array 210 can be an x-by-y-by-z voxel array.

In various instances, the sagittally-captured voxel array 210 can, as its name suggests, have been captured or generated according to the sagittal slicing direction of the set of slicing directions 108. Thus, the sagittally-captured voxel array 210 can be considered as being made up of a set of 2D sagittal slices 212, where each of the set of 2D sagittal slices 212 can be a two-dimensional pixel array that is orthogonal to the sagittal slicing direction. Since the sagittal slicing direction can extend along a right-to-left axis, each of the set of 2D sagittal slices 212 can be an y-by-z slice of the sagittally-captured voxel array 210, and there can be a total of x of such slices: a 2D sagittal slice 212(1) to a 2D sagittal slice 212($x$).

Note that, because the sagittally-captured voxel array 210 can have been captured or generated according to the sagittal slicing direction, the sagittally-captured voxel array 210 can exhibit better spatial resolution, clarity, or detail in directions that are orthogonal to the sagittal slicing direction. Accordingly, if the object 106 is primarily or chiefly oriented along the sagittal slicing direction, the object 106 can be poorly visually perceptible in the sagittally-captured voxel array 210. On the other hand, if the object 106 is primarily or chiefly oriented along the axial or coronal slicing directions, the object 106 can be well visually perceptible in the sagittally-captured voxel array 210.

Referring back to FIG. 1, it can be desired to localize the object 106 within the set of 3D voxel arrays 104. As described herein, the localization system 102 can facilitate such localization.

In various embodiments, the localization system 102 can comprise a processor 110 (e.g., computer processing unit, microprocessor) and a non-transitory computer-readable memory 112 that is operably or operatively or communicatively connected or coupled to the processor 110. The non-transitory computer-readable memory 112 can store computer-executable instructions which, upon execution by the processor 110, can cause the processor 110 or other components of the localization system 102 (e.g., access component 114, model component 116, display component 118) to perform one or more acts. In various embodiments, the non-transitory computer-readable memory 112 can store computer-executable components (e.g., access component 114, model component 116, display component 118), and the processor 110 can execute the computer-executable components.

In various embodiments, the localization system 102 can comprise an access component 114. In various aspects, the access component 114 can electronically receive or otherwise electronically access the set of 3D voxel arrays 104. In various instances, the access component 114 can electronically retrieve the set of 3D voxel arrays 104 from any suitable centralized or decentralized data structures (not shown) or from any suitable centralized or decentralized computing devices (not shown). As a non-limiting example, the access component 114 can electronically retrieve the set of 3D voxel arrays 104 from whatever imaging equipment (e.g., CT scanner, X-ray scanner, MRI scanner, ultrasound scanner, PET scanner) captured or generated the set of 3D voxel arrays 104. In any case, the access component 114 can electronically obtain or access the set of 3D voxel arrays 104, such that other components of the localization system 102 can electronically interact with the set of 3D voxel arrays 104.

In various embodiments, the localization system 102 can comprise a model component 116. In various aspects, as described herein, the model component 116 can execute a deep learning ensemble on the set of 3D voxel arrays 104, thereby yielding a set of two-dimensional object location indicators and a set of confidence scores.

In various embodiments, the localization system 102 can comprise a display component 118. In various instances, as described herein, the display component 118 can visually render any of the two-dimensional object location indicators produced by the deep learning ensemble, based on the confidence scores produced by the deep learning ensemble.

Figure 3:
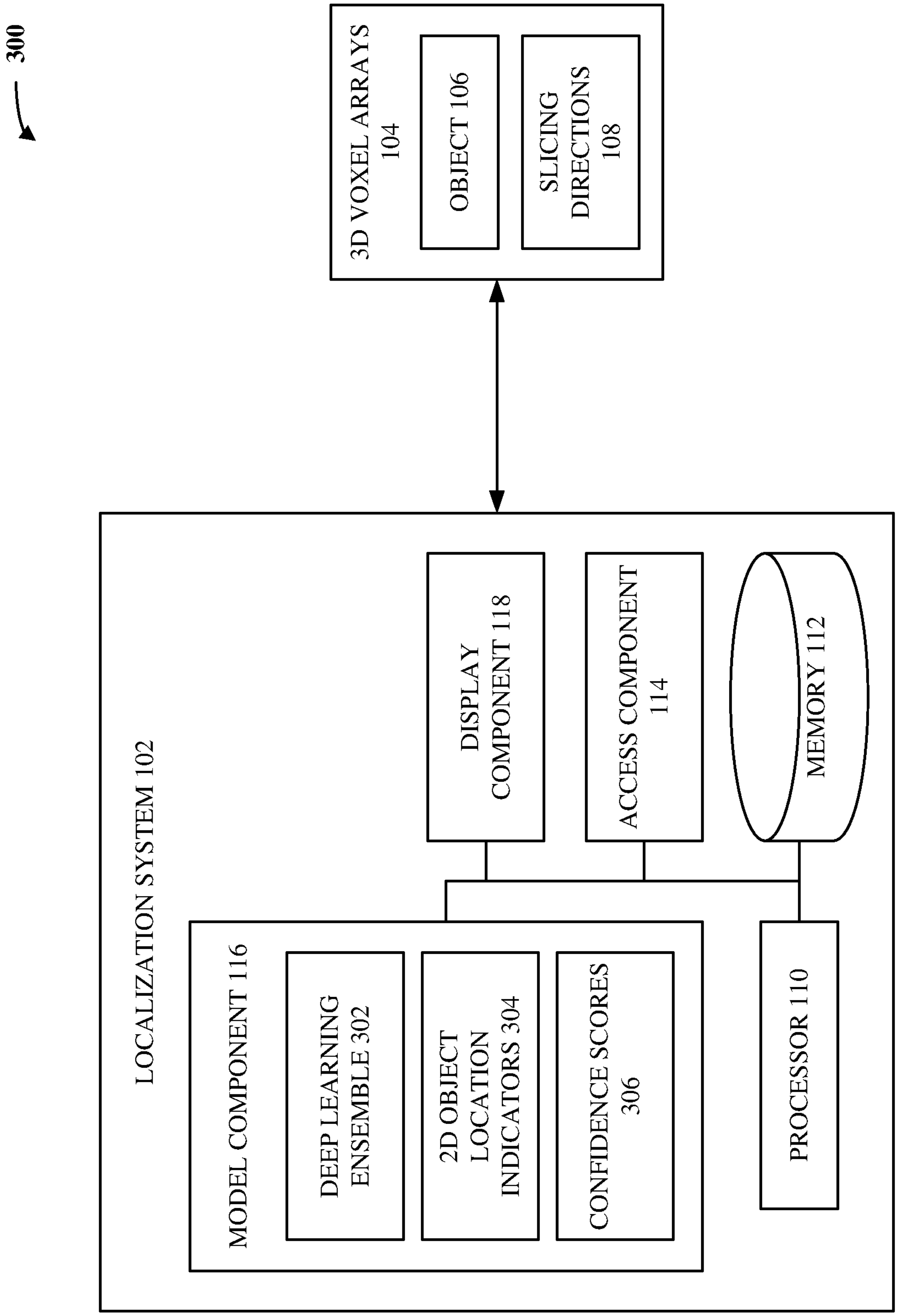
FIG. 3 illustrates a block diagram of an example, non-limiting system including a deep learning ensemble, a set of two-dimensional object location indicators, and a set of confidence scores that facilitates hybrid 3D-to-2D slice-wise object localization ensembles in accordance with one or more embodiments described herein.

FIG. 3 illustrates a block diagram of an example, non-limiting system 300 including a deep learning ensemble, a set of two-dimensional object location indicators, and a set of confidence scores that can facilitate hybrid 3D-to-2D slice-wise object localization ensembles in accordance with one or more embodiments described herein. As shown, the system 300 can, in various cases, comprise the same components as the system 100, and can further comprise a deep learning ensemble 302, a set of 2D object location indicators 304, and a set of confidence scores 306.

In various embodiments, the model component 116 can electronically store, electronically maintain, electronically control, or otherwise electronically access the deep learning ensemble 302. In various aspects, for each given one of the set of slicing directions 108, the deep learning ensemble 302 can include a respective deep learning neural network that is configured or trained to process voxel arrays that are captured or generated according to that given slicing direction. Accordingly, the deep learning ensemble 302 can comprise a respective deep learning neural network for each unique or distinct one of the set of 3D voxel arrays 104. In various instances, the model component 116 can electronically execute the deep learning ensemble 302 on the set of 3D voxel arrays 104, and such execution can cause the deep learning ensemble 302 to produce the set of 2D object location indicators 304 and the set of confidence scores 306. Non-limiting aspects are described with respect to FIGS. 4-5.

Figure 4:
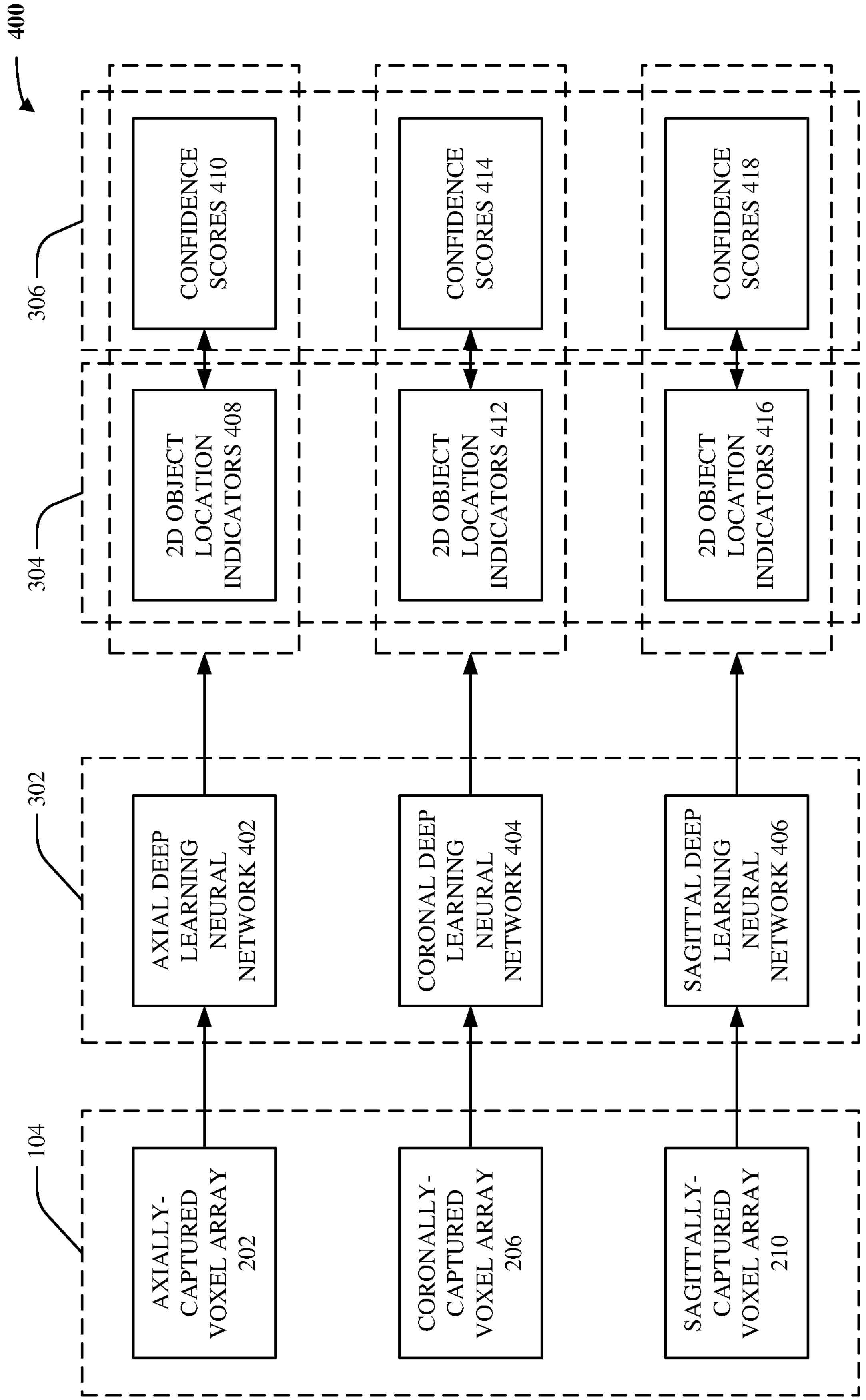
FIGS. 4-5 illustrate example, non-limiting block diagrams showing how a deep learning ensemble can generate two-dimensional object location indicators and confidence scores based on three-dimensional voxel arrays in accordance with one or more embodiments described herein.
Figure 5:
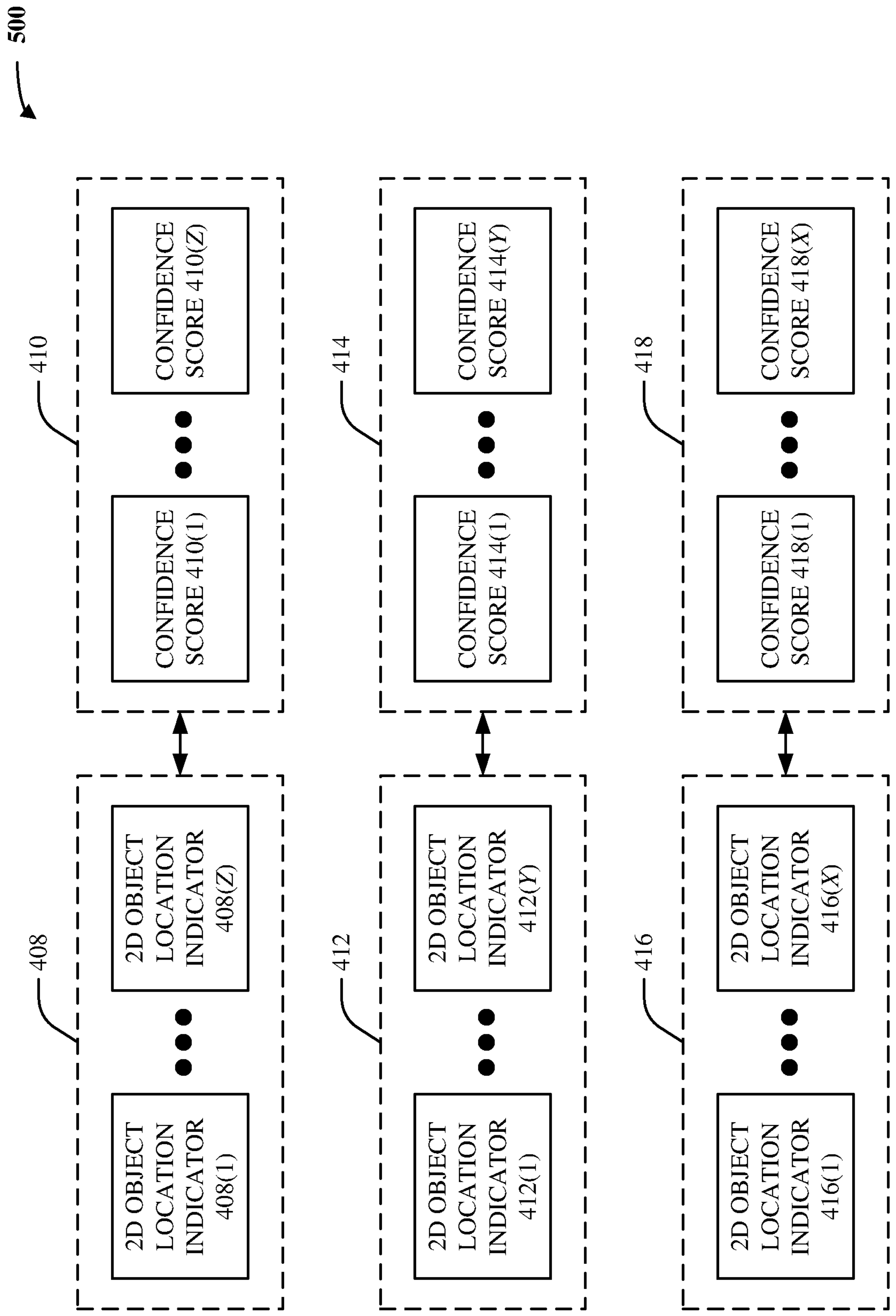

FIGS. 4-5 illustrate example, non-limiting block diagrams 400 and 500 showing how the deep learning ensemble 302 can generate the set of 2D object location indicators 304 and the set of confidence scores 306 based on the set of 3D voxel arrays 104 in accordance with one or more embodiments described herein.

As mentioned above, the deep learning ensemble 302 can comprise a unique or distinct deep learning neural network for each of the set of 3D voxel arrays 104. Because the set of 3D voxel arrays 104 can, in various aspects, comprise three voxel arrays (e.g., 202, 206, and 210), the deep learning ensemble 302 can likewise comprise three deep learning neural networks, one for each of those three voxel arrays. In particular, the deep learning ensemble 302 can comprise an axial deep learning neural network 402 which can be considered as corresponding to the axially-captured voxel array 202, a coronal deep learning neural network 404 which can be considered as corresponding to the coronally-captured voxel array 206, and a sagittal deep learning neural network 406 which can be considered as corresponding to the sagittally-captured voxel array 210.

In various aspects, the deep learning neural networks of the deep learning ensemble 302 can all be arranged in parallel with each other. Moreover, in various cases, each deep learning neural network of the deep learning ensemble 302 can exhibit any suitable internal architecture. For instance, each of the axial deep learning neural network 402, the coronal deep learning neural network 404, and the sagittal deep learning neural network 406 can have an input layer, one or more hidden layers, and an output layer. In various instances, any of such layers can be coupled together by any suitable interneuron connections or interlayer connections, such as forward connections, skip connections, or recurrent connections. Furthermore, in various cases, any of such layers can be any suitable types of neural network layers having any suitable learnable or trainable internal parameters. For example, any of such input layer, one or more hidden layers, or output layer can be convolutional layers, whose learnable or trainable parameters can be convolutional kernels. As another example, any of such input layer, one or more hidden layers, or output layer can be dense layers, whose learnable or trainable parameters can be weight matrices or bias values. As still another example, any of such input layer, one or more hidden layers, or output layer can be batch normalization layers, whose learnable or trainable parameters can be shift factors or scale factors. Further still, in various cases, any of such layers can be any suitable types of neural network layers having any suitable fixed or non-trainable internal parameters. For example, any of such input layer, one or more hidden layers, or output layer can be non-linearity layers, padding layers, pooling layers, or concatenation layers.

In any case, each deep learning neural network of the deep learning ensemble 302 can be configured to receive as input an x-by-y-by-z voxel array that has been captured or generated according to a respective one of the set of slicing directions 108, and to produce as output a two-dimensional object location indicator and confidence score for each slice of that x-by-y-by-z voxel array. Accordingly, the model component 116 can electronically execute a respective deep learning neural network of the deep learning ensemble 302 on each of the set of 3D voxel arrays 104, and such executions, which can occur in parallel with each other, can collectively yield the set of 2D object location indicators 304 and the set of confidence scores 306.

Indeed, in various aspects, the model component 116 can electronically execute the axial deep learning neural network 402 on the axially-captured voxel array 202, and such execution can yield a subset of 2D object location indicators 408 and a subset of confidence scores 410. More specifically, as mentioned above, the axially-captured voxel array 202 can be considered as being made up of the set of 2D axial slices 204. In various aspects, the model component 116 can feed the axially-captured voxel array 202 (e.g., can feed the set of 2D axial slices 204) to an input layer of the axial deep learning neural network 402. In various aspects, the axially-captured voxel array 202 (e.g., the set of 2D axial slices 204) can complete a forward pass through one or more hidden layers of the axial deep learning neural network 402. In various instances, an output layer of the axial deep learning neural network 402 can compute or otherwise calculate the subset of 2D object location indicators 408 and the subset of confidence scores 410 based on activation maps generated by the one or more hidden layers of the axial deep learning neural network 402.

In various aspects, the subset of 2D object location indicators 408 can respectively correspond (e.g., in one-to-one fashion) to the set of 2D axial slices 204. Indeed, as shown in FIG. 5, because the set of 2D axial slices 204 can comprise a total of z slices, the subset of 2D object location indicators 408 can likewise comprise a total of z indicators: a 2D object location indicator 408(1) to a 2D object location indicator 408(*z*). In various instances, each of the subset of 2D object location indicators 408 can be any suitable electronic data that can specify or otherwise convey where, within or inside of a respective one of the set of 2D axial slices 204, the axial deep learning neural network 402 has predicted or inferred that the object 106, or a portion thereof, is located. As a non-limiting example, the 2D object location indicator 408(1) can be a pixel-wise segmentation mask or a two-dimensional bounding box that can indicate or convey where the object 106, or a portion thereof, has been predicted or inferred to be positioned within the 2D axial slice 204(1). As another non-limiting example, the 2D object location indicator 408(*z*) can be a pixel-wise segmentation mask or a two-dimensional bounding box that can indicate or convey where the object 106, or a portion thereof, has been predicted or inferred to be positioned within the 2D axial slice 204(*z*). Note that, in various instances, the z indicators that make up the subset of 2D object location indicators 408 can (e.g., if they were spatially stacked together) be considered as collectively approximating a three-dimensional object location indicator for the axially-captured voxel array 202.

In various aspects, the subset of confidence scores 410 can respectively correspond (e.g., in one-to-one fashion) to the subset of 2D object location indicators 408. Accordingly, since the subset of 2D object location indicators 408 can comprise a total of z indicators, the subset of confidence scores 410 can comprise a total of z confidence scores: a confidence score 410(1) to a confidence score 410(*z*). In various instances, each of the subset of confidence scores 410 can be any suitable scalar whose magnitude (e.g., ranging from 0 to 1) can be considered as indicating, conveying, or representing how much confidence or certainty the axial deep learning neural network 402 has in a respective one of the subset of 2D object location indicators 408. As a non-limiting example, the confidence score 410(1) can indicate or convey a level of confidence or certainty associated with the 2D object location indicator 408(1). As another non-limiting example, the confidence score 410(*z*) can indicate or convey a level of confidence or certainty associated with the 2D object location indicator 408(*z*).

Referring back to FIG. 4, the model component 116 can, in various aspects, electronically execute the coronal deep learning neural network 404 on the coronally-captured voxel array 206, and such execution can yield a subset of 2D object location indicators 412 and a subset of confidence scores 414. In particular, as mentioned above, the coronally-captured voxel array 206 can be considered as being made up of the set of 2D coronal slices 208. In various aspects, the model component 116 can feed the coronally-captured voxel array 206 (e.g., can feed the set of 2D coronal slices 208) to an input layer of the coronal deep learning neural network 404. In various aspects, the coronally-captured voxel array 206 (e.g., the set of 2D coronal slices 208) can complete a forward pass through one or more hidden layers of the coronal deep learning neural network 404. In various instances, an output layer of the coronal deep learning neural network 404 can compute or otherwise calculate the subset of 2D object location indicators 412 and the subset of confidence scores 414 based on activation maps generated by the one or more hidden layers of the coronal deep learning neural network 404.

In various aspects, the subset of 2D object location indicators 412 can respectively correspond (e.g., in one-to-one fashion) to the set of 2D coronal slices 208. Indeed, as shown in FIG. 5, because the set of 2D coronal slices 208 can comprise a total of y slices, the subset of 2D object location indicators 412 can likewise comprise a total of y indicators: a 2D object location indicator 412(1) to a 2D object location indicator 412(*y*). In various instances, each of the subset of 2D object location indicators 412 can be any suitable electronic data that can specify or otherwise convey where, within or inside of a respective one of the set of 2D coronal slices 208, the coronal deep learning neural network 404 has predicted or inferred that the object 106, or a portion thereof, is located. As a non-limiting example, the 2D object location indicator 412(1) can be a pixel-wise segmentation mask or a two-dimensional bounding box that can indicate or convey where the object 106, or a portion thereof, has been predicted or inferred to be positioned within the 2D coronal slice 208(1). As another non-limiting example, the 2D object location indicator 412(*y*) can be a pixel-wise segmentation mask or a two-dimensional bounding box that can indicate or convey where the object 106, or a portion thereof, has been predicted or inferred to be positioned within the 2D coronal slice 208(*y*). Note that, in various instances, the y indicators that make up the subset of 2D object location indicators 412 can (e.g., if they were spatially stacked together) be considered as collectively approximating a three-dimensional object location indicator for the coronally-captured voxel array 206.

In various aspects, the subset of confidence scores 414 can respectively correspond (e.g., in one-to-one fashion) to the subset of 2D object location indicators 412. Accordingly, since the subset of 2D object location indicators 412 can comprise a total of y indicators, the subset of confidence scores 414 can comprise a total of y confidence scores: a confidence score 414(1) to a confidence score 414(*y*). In various instances, each of the subset of confidence scores 414 can be any suitable scalar whose magnitude (e.g., ranging from 0 to 1) can be considered as indicating, conveying, or representing how much confidence or certainty the coronal deep learning neural network 404 has in a respective one of the subset of 2D object location indicators 412. As a non-limiting example, the confidence score 414(1) can indicate or convey a level of confidence or certainty associated with the 2D object location indicator 412(1). As another non-limiting example, the confidence score 414(*y*) can indicate or convey a level of confidence or certainty associated with the 2D object location indicator 412(*y*).

Referring again to FIG. 4, the model component 116 can, in various aspects, electronically execute the sagittal deep learning neural network 406 on the sagittally-captured voxel array 210, and such execution can yield a subset of 2D object location indicators 416 and a subset of confidence scores 418. In particular, as mentioned above, the sagittally-captured voxel array 210 can be considered as being made up of the set of 2D sagittal slices 212. In various aspects, the model component 116 can feed the sagittally-captured voxel array 210 (e.g., can feed the set of 2D sagittal slices 212) to an input layer of the sagittal deep learning neural network 406. In various aspects, the sagittally-captured voxel array 210 (e.g., the set of 2D sagittal slices 212) can complete a forward pass through one or more hidden layers of the sagittal deep learning neural network 406. In various instances, an output layer of the sagittal deep learning neural network 406 can compute or otherwise calculate the subset of 2D object location indicators 416 and the subset of confidence scores 418 based on activation maps generated by the one or more hidden layers of the sagittal deep learning neural network 406.

In various aspects, the subset of 2D object location indicators 416 can respectively correspond (e.g., in one-to-one fashion) to the set of 2D sagittal slices 212. Indeed, as shown in FIG. 5, because the set of 2D sagittal slices 212 can comprise a total of x slices, the subset of 2D object location indicators 416 can likewise comprise a total of x indicators: a 2D object location indicator 416(1) to a 2D object location indicator 416(*x*). In various instances, each of the subset of 2D object location indicators 416 can be any suitable electronic data that can specify or otherwise convey where, within or inside of a respective one of the set of 2D sagittal slices 212, the sagittal deep learning neural network 406 has predicted or inferred that the object 106, or a portion thereof, is located. As a non-limiting example, the 2D object location indicator 416(1) can be a pixel-wise segmentation mask or a two-dimensional bounding box that can indicate or convey where the object 106, or a portion thereof, has been predicted or inferred to be positioned within the 2D sagittal slice 212(1). As another non-limiting example, the 2D object location indicator 416(*x*) can be a pixel-wise segmentation mask or a two-dimensional bounding box that can indicate or convey where the object 106, or a portion thereof, has been predicted or inferred to be positioned within the 2D sagittal slice 212(*x*). Note that, in various instances, the x indicators that make up the subset of 2D object location indicators 416 can (e.g., if they were spatially stacked together) be considered as collectively approximating a three-dimensional object location indicator for the sagittally-captured voxel array 210.

In various aspects, the subset of confidence scores 418 can respectively correspond (e.g., in one-to-one fashion) to the subset of 2D object location indicators 416. Accordingly, since the subset of 2D object location indicators 416 can comprise a total of x indicators, the subset of confidence scores 418 can comprise a total of x confidence scores: a confidence score 418(1) to a confidence score 418(*x*). In various instances, each of the subset of confidence scores 418 can be any suitable scalar whose magnitude (e.g., ranging from 0 to 1) can be considered as indicating, conveying, or representing how much confidence or certainty the sagittal deep learning neural network 406 has in a respective one of the subset of 2D object location indicators 416. As a non-limiting example, the confidence score 418(1) can indicate or convey a level of confidence or certainty associated with the 2D object location indicator 416(1). As another non-limiting example, the confidence score 418(*x*) can indicate or convey a level of confidence or certainty associated with the 2D object location indicator 416(*x*).

In various aspects, the subset of 2D object location indicators 408, the subset of 2D object location indicators 412, and the subset of 2D object location indicators 416 can be considered as collectively forming the set of 2D object location indicators 304. Likewise, the subset of confidence scores 410, the subset of confidence scores 414, and the subset of confidence scores 418 can be considered as collectively forming the set of confidence scores 306.

In various embodiments, it can be possible for the set of 3D voxel arrays 104 to have fewer than three voxel arrays. In particular, it can be the case that one or two of the axially-captured voxel array 202, the coronally-captured voxel array 206, or the sagittally-captured voxel array 210 can be missing or otherwise unavailable (e.g., due to concerns of exposing patients to excessive radiation, or due to hardware limitations of whatever imaging equipment captured or generated the set of 3D voxel arrays 104). In such cases, the model component 116 can execute fewer than all three deep learning neural networks in the deep learning ensemble 302. As a non-limiting example, suppose that the sagittally-captured voxel array 210 were missing or unavailable. In such case, the model component 116 can generate the set of 2D object location indicators 304 and the set of confidence scores 306 by executing the axial deep learning neural network 402 and the coronal deep learning neural network 404, and by letting the sagittal deep learning neural network 406 sit idle (e.g., such idleness would cause 416 and 418 to not be generated). As another non-limiting example, suppose instead that the axially-captured voxel array 202 and the coronally-captured voxel array 206 were missing or unavailable. In such case, the model component 116 can generate the set of 2D object location indicators 304 and the set of confidence scores 306 by executing the sagittal deep learning neural network 406, and by letting the axial deep learning neural network 402 and the coronal deep learning neural network 404 sit idle (e.g., such idleness would cause 408, 410, 412, and 414 to not be generated). Localization accuracy can be somewhat reduced when fewer than all three of the axially-captured voxel array 202, the coronally-captured voxel array 206, and the sagittally-captured voxel array 210 are available (e.g., again, such different voxel arrays can have different in-plane resolutions, which means that the object 106 might be more easily or accurately localizable in some of such three voxel arrays than in others). However, the fact that some deep learning neural networks of the deep learning ensemble 302 can sit idle demonstrates how flexible the deep learning ensemble 302 can be. In other words, it is not necessary to always have all three of the axially-captured voxel array 202, the coronally-captured voxel array 206, and the sagittally-captured voxel array 210 available to localize the object 106. Indeed, such localization can nevertheless be performed (albeit with a chance of slightly reduced accuracy), even if one or two of such three voxel arrays are missing or unavailable.

In any case, as described herein, each deep learning neural network (e.g., 402, 404, and 406) of the deep learning ensemble 302 can generate two-dimensional outputs (e.g., 408, 412, 416) based on three-dimensional inputs (e.g., 202, 206, 210). Accordingly, each deep learning neural network of the deep learning ensemble 302 can be considered as exhibiting a hybrid 3D-to-2D slice-wise configuration. In various aspects, such hybrid 3D-to-2D slice-wise configuration can be accomplished or otherwise implemented by causing each deep learning neural network of the deep learning ensemble 302 to comprise some layers that are operable on three-dimensional data and to also comprise other layers that are operable on two-dimensional data.

For instance, each deep learning neural network in the deep learning ensemble 302 can comprise any suitable number of upstream layers that implement three-dimensional convolutional kernels, can comprise any suitable number of downstream layers that instead implement two-dimensional convolutional kernels, and can refrain from performing resizing or resampling operations along a respective slicing direction (e.g., the axial deep learning neural network 402 can refrain from resizing or resampling along the axial slicing direction; the coronal deep learning neural network 404 can refrain from resizing or resampling along the coronal slicing direction; the sagittal deep learning neural network 406 can refrain from resizing or resampling along the sagittal slicing direction). In such cases, the upstream layers can receive as input a respective voxel array (e.g., 202, 206, or 210) and can process that voxel array with three-dimensional convolutional kernels, thereby yielding three-dimensional hidden activation maps (not shown). Because resizing or resampling can be refrained or avoided along whatever slicing direction is at issue, those three-dimensional hidden activation maps can be made up of the same number of two-dimensional slices as the inputted voxel array (e.g., the three-dimensional hidden activation maps of the axial deep learning neural network 402 can each have a total of z slices, just like the axially-captured voxel array 202; the three-dimensional hidden activation maps of the coronal deep learning neural network 404 can each have a total of y slices, just like the coronally-captured voxel array 206; the three-dimensional hidden activation maps of the sagittal deep learning neural network 406 can each have a total of x slices, just like the sagittally-captured voxel array 210). Accordingly, in various aspects, the downstream layers can be applied on a slice-wise basis to those three-dimensional hidden activation maps (e.g., can be applied in parallel, via weight sharing, to each two-dimensional slice of those three-dimensional hidden activation maps), so as to produce a two-dimensional object location indicator and a corresponding confidence score for each two-dimensional slice of the inputted voxel array. A non-limiting example of such a hybrid 3D-to-2D slice-wise configuration is described with respect to FIG. 6.

Figure 6:
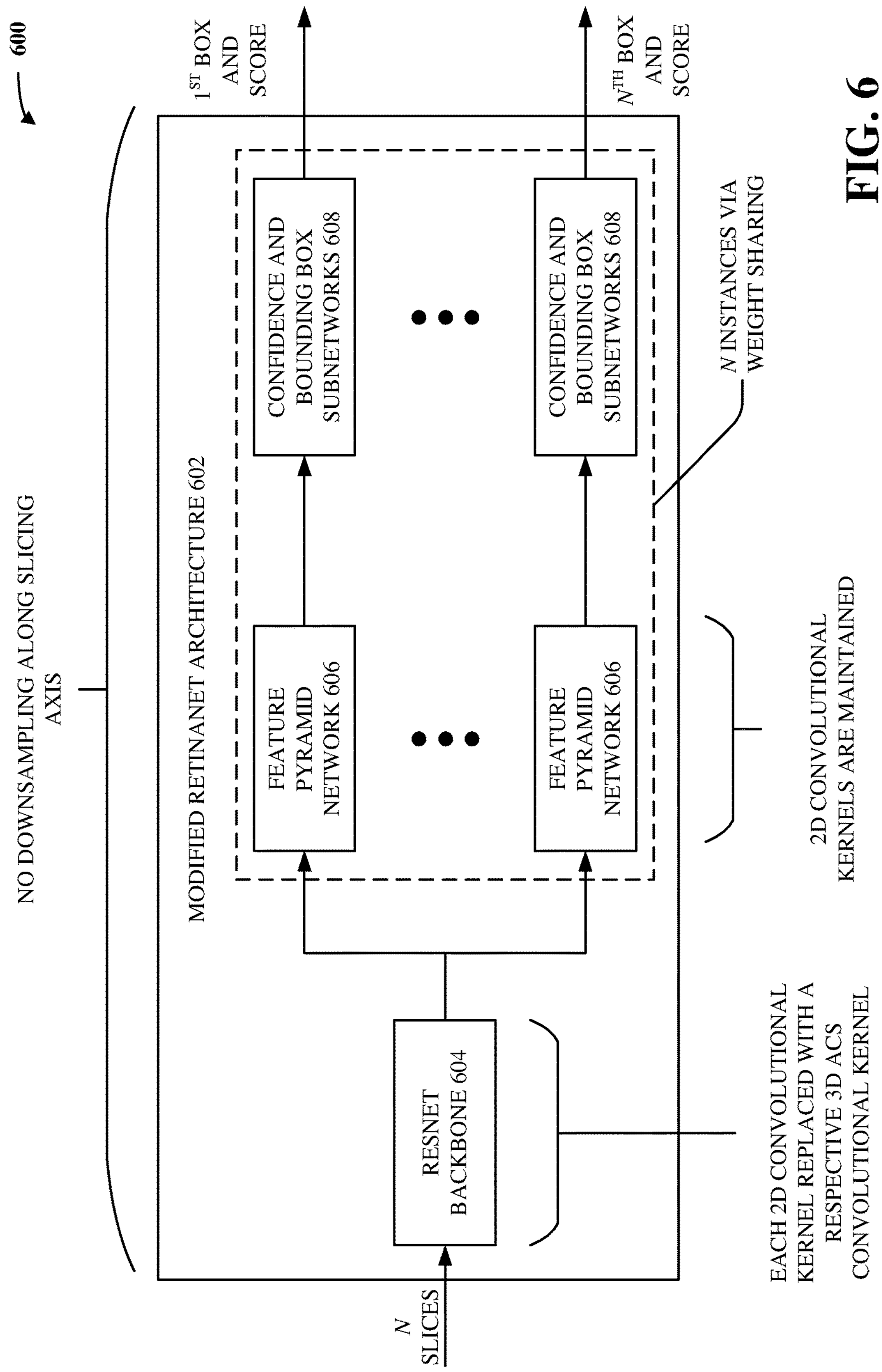
FIG. 6 illustrates an example, non-limiting block diagram showing a modified RetinaNet architecture that can be implemented in a deep learning ensemble in accordance with one or more embodiments described herein.

FIG. 6 illustrates an example, non-limiting block diagram 600 showing a modified RetinaNet architecture that can be implemented in a deep learning ensemble in accordance with one or more embodiments described herein. Such a modified RetinaNet architecture can be considered as facilitating a hybrid 3D-to-2D slice-wise configuration.

In various embodiments, each deep learning neural network of the deep learning ensemble 302 can exhibit a modified RetinaNet architecture 602. In various aspects, as shown, the modified RetinaNet architecture 602 can comprise a ResNet backbone 604, a Feature Pyramid Network 606 (hereafter "FPN 606"), and confidence and bounding box subnetworks 608.

In various instances, all downsampling operations (or upsampling operations) throughout the modified RetinaNet architecture 602 can be configured or otherwise set to not perform downsampling (or upsampling) along a respective one of the set of slicing directions 108. With respect to the axial deep learning neural network 402 (e.g., if the axial deep learning neural network 402 is constructed in accordance with the modified RetinaNet architecture 602), the downsampling operations of the modified RetinaNet architecture 602 can refrain from downsampling along the axial slicing direction and can instead downsample along the coronal and sagittal slicing directions. With respect to the coronal deep learning neural network 404 (e.g., if the coronal deep learning neural network 404 is constructed in accordance with the modified RetinaNet architecture 602), the downsampling operations of the modified RetinaNet architecture 602 can refrain from downsampling along the coronal slicing direction and can instead downsample along the axial and sagittal slicing directions. Likewise, with respect to the sagittal deep learning neural network 406 (e.g., if the sagittal deep learning neural network 406 is constructed in accordance with the modified RetinaNet architecture 602), the downsampling operations of the modified RetinaNet architecture 602 can refrain from downsampling along the sagittal slicing direction and can instead downsample along the axial and coronal slicing directions.

In various instances, the ResNet backbone 604 can exhibit any suitable ResNet architecture, except that the ResNet backbone 604 can comprise three-dimensional convolutional kernels instead of two-dimensional convolutional kernels. As a non-limiting example, the ResNet backbone 604 can begin as a traditional ResNet architecture, and each two-dimensional convolutional kernel of that traditional ResNet architecture can be converted into a respective three-dimensional format, via implementation of the 3D ACS kernel conversion technique.

In various aspects, the FPN 606 can be downstream of the ResNet backbone 604 and can exhibit any traditional FPN architecture. That is, the FPN 606 can comprise two-dimensional convolutional kernels instead of three-dimensional convolutional kernels. Similarly, the confidence and bounding box subnetworks 608 can be downstream of the FPN 606 and can exhibit any traditional architectures. However, as shown, the FPN 606 and the confidence and bounding box subnetworks 608 can be applied in parallel, via weight sharing, on a slice-wise basis. This can be due to the fact that downsampling operations (or upsampling operations) throughout the modified RetinaNet architecture 602 can refrain from performing any downsampling (or upsampling) along a respective one of the set of slicing directions 108.

As a non-limiting example, the ResNet backbone 604 can, as shown, receive as input a voxel array that can be considered as a sequence of n two-dimensional slices, for any suitable positive integer n. With respect to the axial deep learning neural network 402, n can be equal to z. With respect to the coronal deep learning neural network 404, n can be equal to y. With respect to the sagittal deep learning neural network 406, n can be equal to x. In any case, the ResNet backbone 604 can utilize its three-dimensional convolutional kernels to process all of such n slices simultaneously (e.g., so as to take into account interslice contextual information present in the n slices). This can cause the ResNet backbone 604 to produce various three-dimensional hidden activation maps (not shown). Because no downsampling (or upsampling) can be performed along the applicable slicing direction (e.g., axial slicing direction for 402, coronal slicing direction for 404, sagittal slicing direction for 406), the three-dimensional hidden activation maps produced by the ResNet backbone 604 can be considered as each comprising n two-dimensional slices. Accordingly, the FPN 606 and the confidence and bounding box subnetworks 608 can be applied, via weight sharing, on a slice-wise basis to those three-dimensional hidden activation maps. For example, a first instance of the FPN 606 and of the confidence and bounding box subnetworks 608 can be applied to first slices of those three-dimensional hidden activation maps, and the final output produced by that first instance of the FPN 606 and of the confidence and bounding box subnetworks 608 can be a first two-dimensional bounding box and a corresponding first confidence score. As another example, an n-th instance of the FPN 606 and of the confidence and bounding box subnetworks 608 can be applied to n-th slices of those three-dimensional hidden activation maps, and the final output produced by that n-th instance of the FPN 606 and of the confidence and bounding box subnetworks 608 can be an n-th two-dimensional bounding box and a corresponding n-th confidence score. In this way, the modified RetinaNet architecture 602 can receive three-dimensional inputs and can produce slice-wise two-dimensional outputs.

In any case, the model component 116 can generate the set of 2D object location indicators 304 and the set of confidence scores 306, by executing the deep learning ensemble 302 on the set of 3D voxel arrays 104.

In various embodiments, the display component 118 can electronically perform any suitable actions, based on the set of confidence scores 306.

As a non-limiting example, the display component 118 can, in various aspects, present a binary or dichotomous result to a user or operator, based on determining whether at least one of the set of confidence scores 306 satisfies (e.g., exceeds) any suitable threshold value. In particular, in response to determining that none of the set of confidence scores 306 satisfies the threshold value, the display component 118 can electronically render, on any suitable electronic display (e.g., computer screen, computer monitor), an electronic notification, alert, or warning that indicates (e.g., via text) that the object 106 was not detected or localized within any of the set of 3D voxel arrays 104. On the other hand, in response to determining that at least one of the set of confidence scores 306 satisfies the threshold value, the display component 118 can electronically render, on the electronic display, an electronic notification, alert, or warning that indicates (e.g., via text) that the object 106 was detected or localized within at least one of the set of 3D voxel arrays 104.

As another non-limiting example, the display component 118 can, in various aspects, present any of the set of 2D object location indicators 304 to a user or operator, based on determining whether at least one of the set of confidence scores 306 satisfies (e.g., exceeds) the threshold value. Indeed, in response to determining that at least one of the set of confidence scores 306 satisfies the threshold value, the display component 118 can electronically render, on the electronic display, whichever of the set of 2D object location indicators 304 correspond to the at least one confidence score that satisfies the threshold value. Accordingly, the user or operator can visually see whichever 2D object location indicators have been determined to denote or localize the object 106 with sufficient confidence.

Note that, in various instances, the threshold value can be fixed to any suitable default value or can instead be a variable that is defined by user-provided input. As a non-limiting example, a user of the localization system 102 can provide, via any suitable human-computer interface device (not shown), input (not shown) that specifies, selects, or otherwise chooses the particular magnitude of the threshold value. In such cases, the threshold value can be considered as a controllable or adjustable parameter that can be customized depending upon operational context. For instance, suppose that the localization system 102 is implemented in a field or operational context for which the consequences of failing to localize the object 106 are severe (e.g., the object 106 can be a malignant tumor, and failing to localize the malignant tumor can have catastrophic consequences for a medical patient). In such case, to be overcautious or otherwise on the safe side, a user or operator of the localization system 102 can set the threshold value to a lower magnitude (e.g., farther from a 100% confidence threshold), such that even moderately-confident ones of the set of 2D object location indicators 304 are displayed or presented to the user or operator (e.g., if the object 106 is a malignant tumor, the threshold value can be set to 50%, such that any 2D object location indicator that has been determined to be more than 50% likely to denote a malignant tumor is presented to the user or operator). On the other hand, suppose that the localization system 102 is implemented in a field or operational context for which the consequences of failing to localize the object 106 are not severe (e.g., the object 106 can be dental plaque, and failing to localize the dental plaque can have non-catastrophic consequences for a medical patient). In such case, a user or operator of the localization system 102 can set the threshold value to a higher magnitude (e.g., closer to a 100% confidence threshold), such that only highly-confident ones of the set of 2D object location indicators 304 are displayed or presented to the user or operator (e.g., if the object 106 is dental plaque, the threshold value can be set to 95%, such that any 2D object location indicator that has been determined to be more than 95% likely to denote dental plaque is presented to the user or operator).

Figure 7:
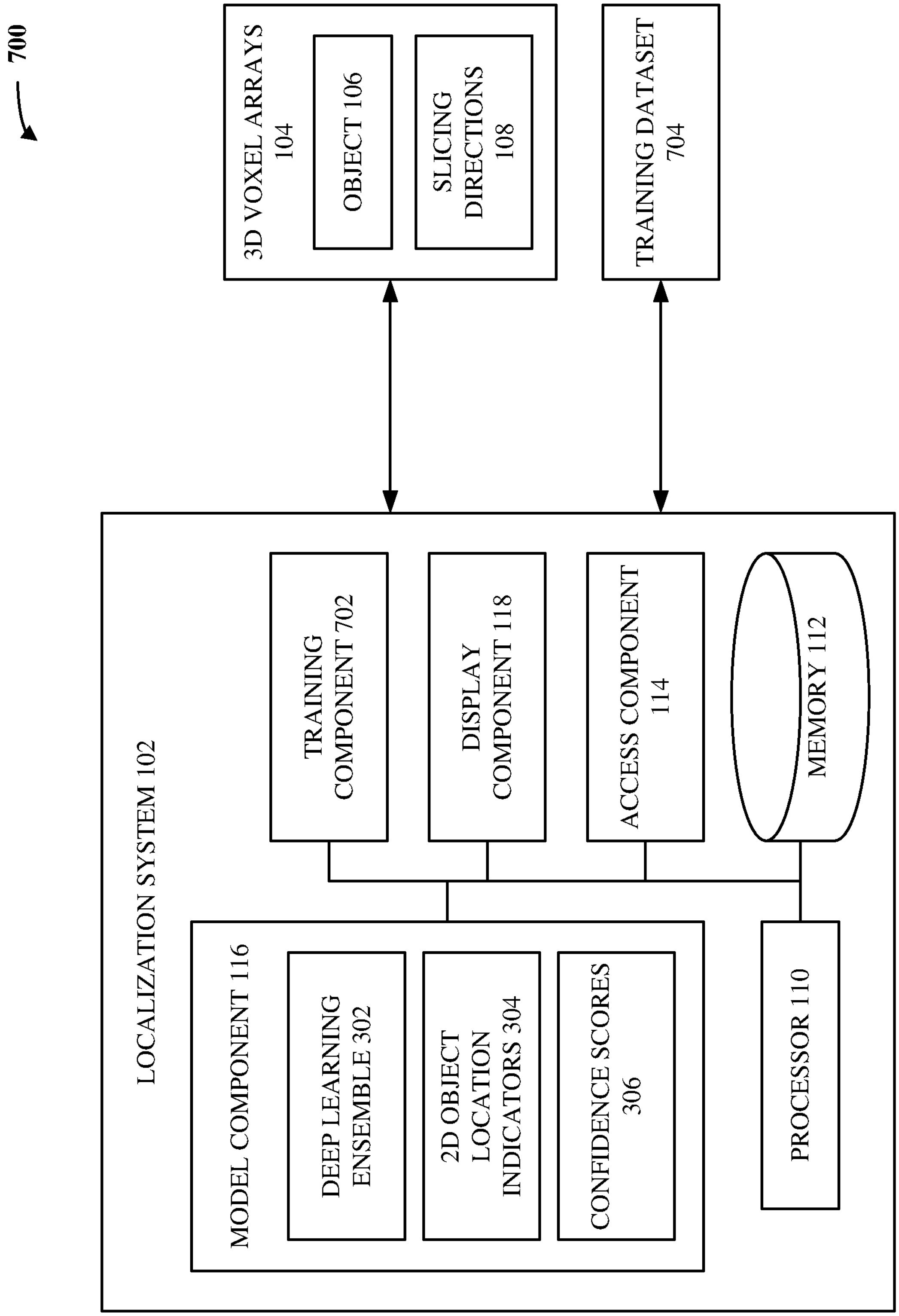
FIG. 7 illustrates a block diagram of an example, non-limiting system including a training component and a training dataset that facilitates hybrid 3D-to-2D slice-wise object localization ensembles in accordance with one or more embodiments described herein.
Figure 8:
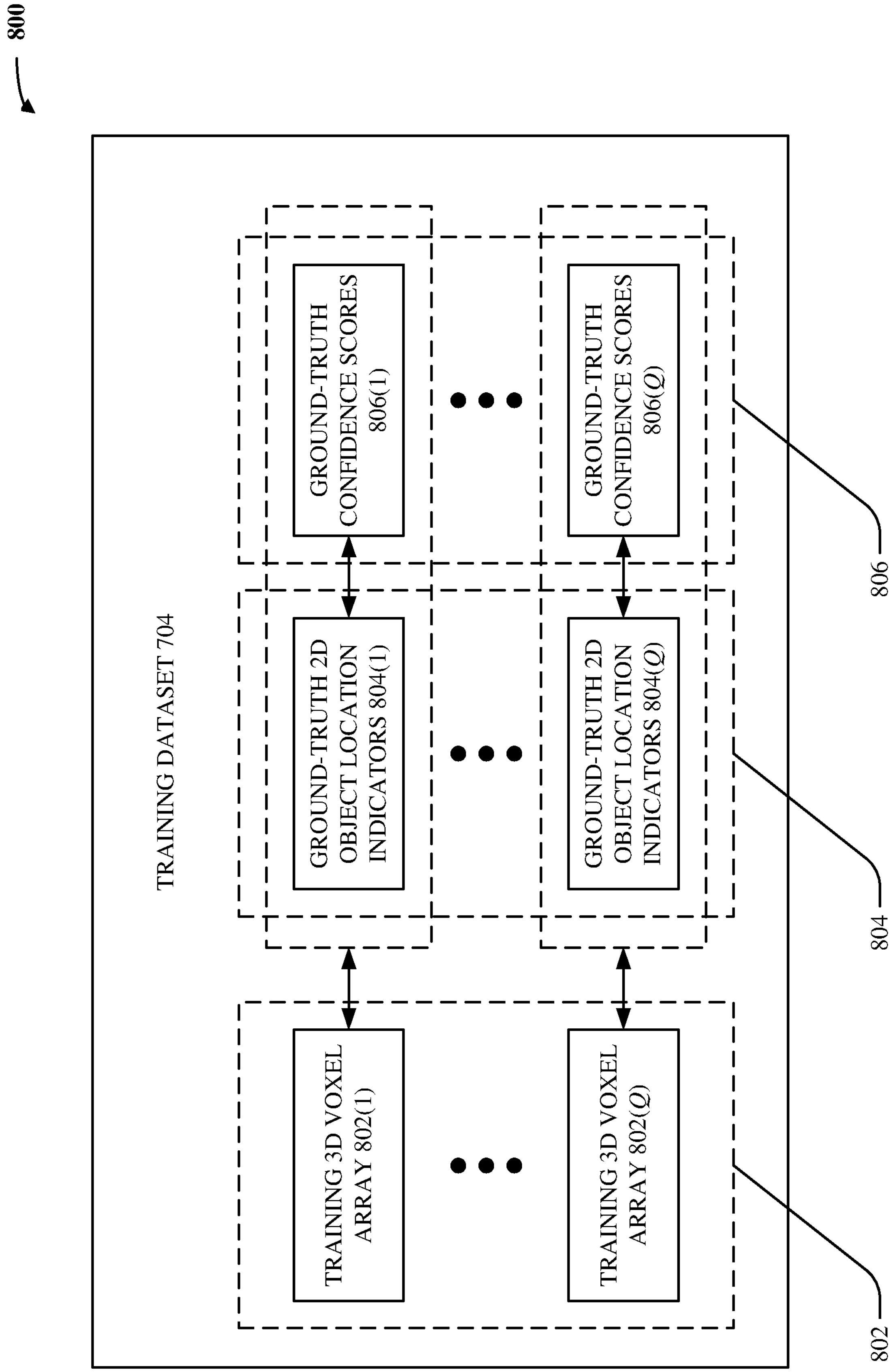
FIG. 8 illustrates an example, non-limiting block diagram of a training dataset in accordance with one or more embodiments described herein.
Figure 9:
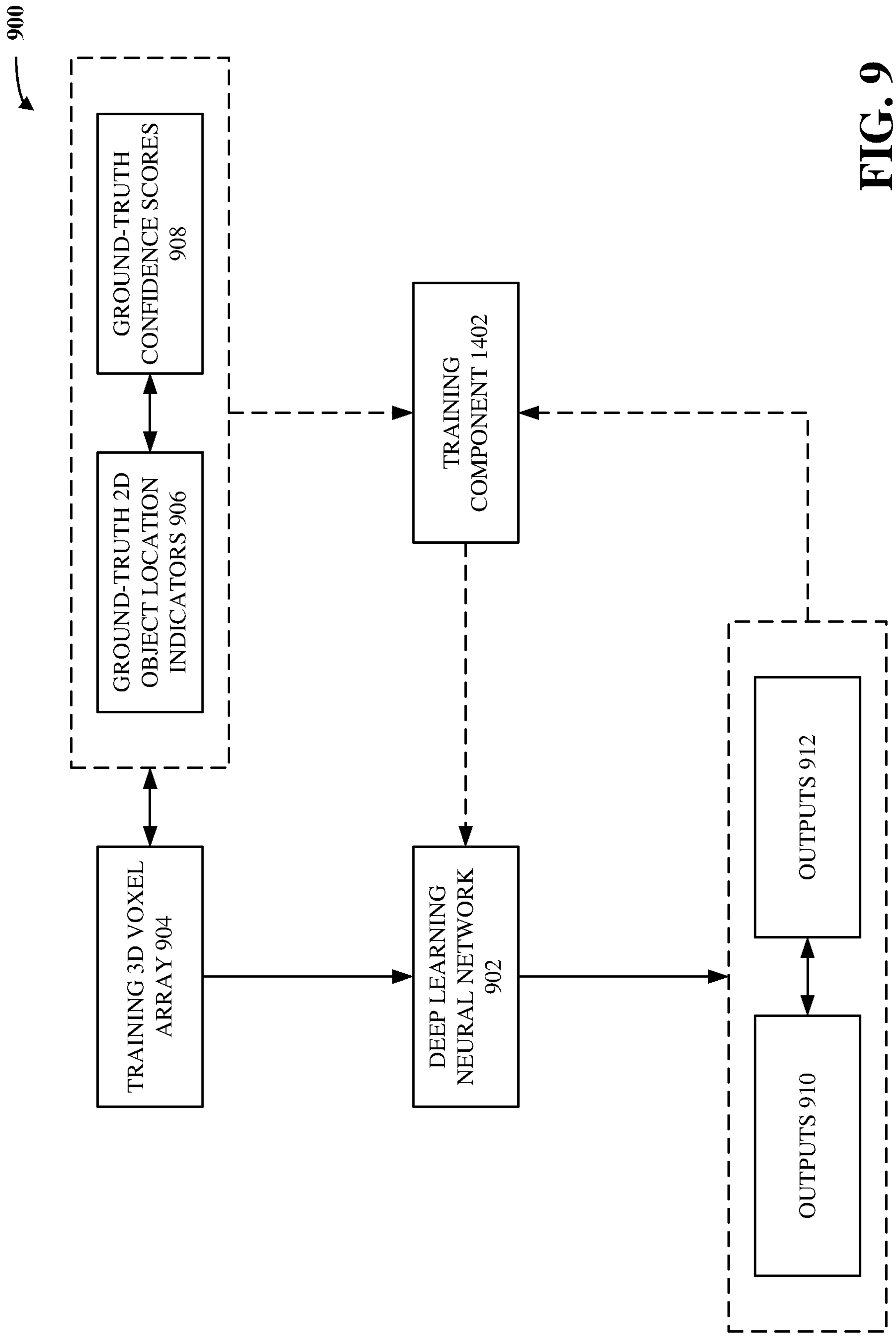
FIG. 9 illustrates an example, non-limiting block diagram showing how individual models of a deep learning ensemble can be trained in accordance with one or more embodiments described herein.

In order for the set of 2D object location indicators 304 and the set of confidence scores 306 to be accurate, each deep learning neural network in the deep learning ensemble 302 can first undergo training, as described with respect to FIGS. 7-9.

FIG. 7 illustrates a block diagram of an example, non-limiting system 700 including a training component and a training dataset that can facilitate hybrid 3D-to-2D slice-wise object localization ensembles in accordance with one or more embodiments described herein. As shown, the system 700 can, in some cases, comprise the same components as the system 300, and can further comprise a training component 702 and a training dataset 704.

In various embodiments, the access component 114 can electronically receive, retrieve, or otherwise access, from any suitable source, the training dataset 704. In various aspects, the training component 702 can train any deep learning neural network of the deep learning ensemble 302 on the training dataset 704. Non-limiting aspects of such training are described with respect to FIGS. 8-9.

FIG. 8 illustrates an example, non-limiting block diagram 800 of the training dataset 704 in accordance with one or more embodiments described herein.

As shown, the training dataset 704 can comprise a set of training 3D voxel arrays 802. In various aspects, the set of training 3D voxel arrays 802 can comprise q arrays for any suitable positive integer q: a training 3D voxel array 802(1) to a training 3D voxel array **802(*q*). In various instances, each of the set of training 3D voxel arrays 802 can exhibit the same format, size, dimensionality, and slicing direction as any given one of the set of 3D voxel arrays 104. For example, if the training dataset 704 is intended for training of the axial deep learning neural network 402, then each of the set of training 3D voxel arrays 802 can exhibit the same format, size, dimensionality, and slicing direction as the axially-captured voxel array 202 (e.g., each of the set of training 3D voxel arrays 802 can be a sequence of z slices, with each slice being an x-by-y pixel array). As another example, if the training dataset 704 is intended for training of the coronal deep learning neural network 404, then each of the set of training 3D voxel arrays 802 can exhibit the same format, size, dimensionality, and slicing direction as the coronally-captured voxel array 206 (e.g., each of the set of training 3D voxel arrays 802 can be a sequence of y slices, with each slice being an x-by-z pixel array). As even another example, if the training dataset 704 is intended for training of the sagittal deep learning neural network 406, then each of the set of training 3D voxel arrays 802 can exhibit the same format, size, dimensionality, and slicing direction as the sagittally-captured voxel array 210 (e.g., each of the set of training 3D voxel arrays 802 can be a sequence of x slices, with each slice being an y-by-z pixel array). In any case, each of the set of training 3D voxel arrays 802 can depict or illustrate an object that is of the same type or class as the object 106** (e.g., positive localization examples) or can depict no such object at all (e.g., negative localization examples).

In various aspects, as shown, the training dataset 704 can comprise a set of subsets of ground-truth 2D object location indicators 804. In various instances, the set of subsets of ground-truth 2D object location indicators 804 can respectively correspond to the set of training 3D voxel arrays 802. Thus, since the set of training 3D voxel arrays 802 can comprise q arrays, the set of subsets of ground-truth 2D object location indicators 804 can comprise q subsets: a subset of ground-truth 2D object location indicators 804(1) to a subset of ground-truth 2D object location indicators **804(*q*). In various cases, each of the set of subsets of ground-truth 2D object location indicators 804 can be considered as being the correct or accurate 2D object location indicators that are known or deemed to correspond to a respective one of the set of training 3D voxel arrays 802. As a non-limiting example, the subset of ground-truth 2D object location indicators 804(1) can be considered as specifying the respective correct or accurate 2D object location indicator (e.g., correct or accurate pixel-wise segmentation mask, correct or accurate two-dimensional bounding box) for each slice of the training 3D voxel array 802(1). As another non-limiting example, the subset of ground-truth 2D object location indicators 804(*q*) can be considered as specifying the respective correct or accurate 2D object location indicator for each slice of the training 3D voxel array 802(*q*)**.

In various instances, as shown, the training dataset 704 can comprise a set of subsets of ground-truth confidence scores 806. In various cases, the set of subsets of ground-truth confidence scores 806 can respectively correspond to the set of subsets of ground-truth 2D object location indicators 804. Thus, since the set of subsets of ground-truth 2D object location indicators 804 can comprise q subsets, the set of subsets of ground-truth confidence scores 806 can likewise comprise q subsets: a subset of ground-truth confidence scores 806(1) to a subset of ground-truth confidence scores **806(*q*). In various aspects, each of the set of subsets of ground-truth confidence scores 806 can be considered as specifying the correct or accurate levels of confidence (e.g., 1, or 100%) that are known or deemed to correspond to a respective one of the set of subsets of ground-truth 2D object location indicators 804. As a non-limiting example, the subset of ground-truth confidence scores 806(1) can specify a respective level of confidence or certainty that is known or deemed to correspond to each of the subset of ground-truth 2D object location indicators 804(1). As another non-limiting example, the subset of ground-truth confidence scores 806(*q*) can specify a respective level of confidence or certainty that is known or deemed to correspond to each of the subset of ground-truth 2D object location indicators 804(*q*)**.

In various embodiments, the localization system 102 can be considered as an accessory or ancillary system that can be implemented in combination with or otherwise to support whatever imaging device captured or generated the set of 3D voxel arrays 104. As a non-limiting example, suppose that the set of 3D voxel arrays 104 are medical scanned images that have been captured, generated, or reconstructed by a medical imaging scanner (e.g., a CT scanner, an MRI scanner, an X-ray scanner, an ultrasound scanner, a PET scanner). Furthermore, suppose that the object 106 is a particular anatomical pathology (e.g., a bone fracture) that might or might not be visually illustrated in the set of 3D voxel arrays 104. In such cases, the localization system 102 can be electronically installed on the medical imaging scanner, so as to automatically localize in real-time that particular anatomical pathology within whatever 3D voxel arrays are produced by the medical imaging scanner. Such automatic, real-time localization can tremendously help to lighten or streamline real-world clinical workflows, especially in situations where attendant medical personnel (e.g., radiologists, surgeons, nurses) that rely on the medical imaging scanner are overworked or short-staffed. In other words, the automatic, real-time localizations produced by the localization system 102 can, in the clinical context, be considered as assisting real-world medical personnel to make quicker or more accurate real-world diagnostic, prognostic, or treatment decisions with respect to real-world medical patients (e.g., automatic, real-time localizations produced by the localization system 102 can allow appropriate medical treatment or intervention to be provided to a medical patient earlier than would otherwise be possible, which can lead to a better medical outcome for the medical patient). Accordingly, the localization system 102 can certainly be considered as a useful and practical application of computer technology.

FIG. 9 illustrates an example, non-limiting block diagram 900 showing how individual models of the deep learning ensemble 302 can be trained based on the training dataset 704 in accordance with one or more embodiments described herein.

In various aspects, there can be a deep learning neural network 902. The deep learning neural network 902 can be any of the deep learning neural networks in the deep learning ensemble 302 (e.g., can be the axial deep learning neural network 402, can be the coronal deep learning neural network 404, can be the sagittal deep learning neural network 406).

In various instances, prior to beginning training, the training component 702 can initialize the internal parameters (e.g., weight matrices, bias vectors, convolutional kernels) of the deep learning neural network 902 in any suitable fashion (e.g., random initialization).

In various cases, as shown, the training component 702 can select from the training dataset 704 a training 3D voxel array 904, a subset of ground-truth 2D object location indicators 906 that correspond to the training 3D voxel array 904, and a subset of ground-truth confidence scores 908 that correspond to the subset of ground-truth 2D object location indicators 906. Note that, if the deep learning neural network 902 is the axial deep learning neural network 402, then the training 3D voxel array 904 can be made up of axial slices, and the subset of ground-truth 2D object location indicators 906 can respectively correspond to those axial slices. Similarly, if the deep learning neural network 902 is the coronal deep learning neural network 404, then the training 3D voxel array 904 can be made up of coronal slices, and the subset of ground-truth 2D object location indicators 906 can respectively correspond to those coronal slices. Likewise, if the deep learning neural network 902 is the sagittal deep learning neural network 406, then the training 3D voxel array 904 can be made up of sagittal slices, and the subset of ground-truth 2D object location indicators 906 can respectively correspond to those sagittal slices.

In various instances, the training component 702 can execute the deep learning neural network 902 on the training 3D voxel array 904. In various cases, this can cause the deep learning neural network 902 to produce outputs 910 and outputs 912. More specifically, the training component 702 can feed the training 3D voxel array 904 to the input layer of the deep learning neural network 902. In various cases, the training 3D voxel array 904 can complete a forward pass through the one or more hidden layers of the deep learning neural network 902. Accordingly, the output layer of the deep learning neural network 902 can compute or calculate the outputs 910 and the outputs 912 based on activation maps produced by the one or more hidden layers of the deep learning neural network 902.

Note that, in various cases, the format, size, or dimensionality of the outputs 910 and of the outputs 912 can be controlled or otherwise determined by the number, arrangement, or sizes of neurons or other internal parameters (e.g., convolutional kernels) that are contained in or that otherwise make up the output layer (or other layers) of the deep learning neural network 902. Thus, the outputs 910 and the outputs 912 can be forced to have any desired format, size, or dimensionality by adding, removing, or otherwise adjusting neurons or other internal parameters to, from, or within the output layer (or other layers) of the deep learning neural network 902.

In any case, the outputs 910 can be considered as being or otherwise specifying a respective predicted or inferred 2D object location indicator that the deep learning neural network 902 has generated for each slice of the training 3D voxel array 904, and the outputs 912 can be considered as being or otherwise specifying a respective predicted or inferred confidence score that the deep learning neural network 902 has produced for each of the outputs 910. In contrast, the subset of ground-truth 2D object location indicators 906 can be considered as being or otherwise specifying the respective correct or accurate 2D object location indicator for each slice of the training 3D voxel array 904, and the subset of ground-truth confidence scores 908 can be considered as being or otherwise specifying the respective correct or accurate confidence score for each of the subset of ground-truth 2D object location indicators 906. Note that, if the deep learning neural network 902 has so far undergone no or little training, then the outputs 910 and the outputs 912 can be highly inaccurate or incorrect (e.g., can be very different from 906 and 908, respectively).

In various aspects, the training component 702 can compute any suitable errors or losses (e.g., mean absolute error, mean squared error, cross-entropy error) between the outputs 910 and the subset of ground-truth 2D object location indicators 906, and between the outputs 912 and the subset of ground-truth confidence scores 908. In various instances, as shown, the training component 702 can incrementally update the trainable internal parameters of the deep learning neural network 902, by performing backpropagation (e.g., stochastic gradient descent) driven by those computed errors or losses.

In various cases, the training component 702 can repeat such training for any suitable number of training 3D voxel arrays. This can ultimately cause the trainable internal parameters of the deep learning neural network 902 to become iteratively optimized for accurately generating slice-wise 2D object location indicators and confidence scores based on inputted voxel arrays. In various aspects, the training component 702 can implement any suitable training batch sizes, any suitable training termination criterion, or any suitable error, loss, or objective function when training the deep learning neural network 902.

Although the herein disclosure has mainly described how the deep learning neural network 902 (e.g., how any of the deep learning neural networks in the deep learning ensemble 302) can be trained in a supervised fashion, this is a mere non-limiting example. In various other embodiments, the deep learning neural network 902 can instead be trained in any other suitable fashion (e.g., via unsupervised learning, via reinforcement learning).

Figure 10:
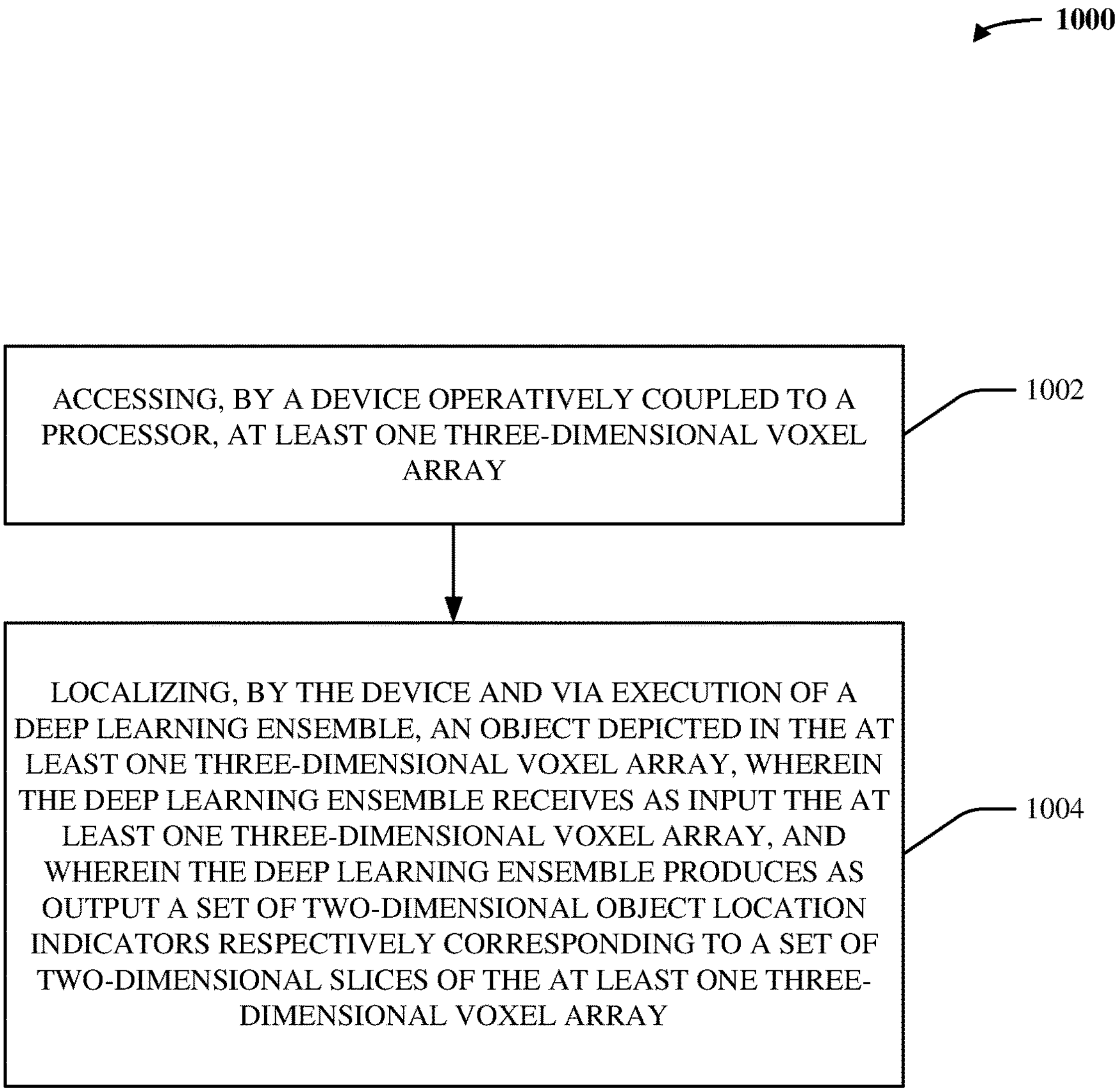
FIG. 10 illustrates a flow diagram of an example, non-limiting computer-implemented method that facilitates hybrid 3D-to-2D slice-wise object localization ensembles in accordance with one or more embodiments described herein.

FIG. 10 illustrates a flow diagram of an example, non-limiting computer-implemented method 1000 that can facilitate hybrid 3D-to-2D slice-wise object localization ensembles in accordance with one or more embodiments described herein. In various cases, the localization system 102 can facilitate the computer-implemented method 1000.

In various embodiments, act 1002 can include accessing, by a device (e.g., via 114) operatively coupled to a processor (e.g., 110), at least one three-dimensional voxel array (e.g., 104).

In various aspects, act 1004 can include localizing, by the device (e.g., via 116) and via execution of a deep learning ensemble (e.g., 302), an object (e.g., 106) depicted in the at least one three-dimensional voxel array. In various instances, the deep learning ensemble can receive as input the at least one three-dimensional voxel array, and the deep learning ensemble can produce as output a set of two-dimensional object location indicators (e.g., 304) respectively corresponding to a set of two-dimensional slices (e.g., 204, 208, 212) of the at least one three-dimensional voxel array.

Although not explicitly shown in FIG. 10, the deep learning ensemble can comprise a first deep learning neural network (e.g., 402), a second deep learning neural network (e.g., 404), and a third deep learning neural network (e.g., 406) that are in parallel with each other; the at least one three-dimensional voxel array can comprise a first three-dimensional voxel array (e.g., 202) made up of axial two-dimensional slices (e.g., 204), a second three-dimensional voxel array (e.g., 206) made up of coronal two-dimensional slices (e.g., 208), and a third three-dimensional voxel array (e.g., 210) made up of sagittal two-dimensional slices (e.g., 212); the first deep learning neural network can receive as input the first three-dimensional voxel array and can produce as output, for each of the axial two-dimensional slices of the first three-dimensional voxel array, a respective one of the set of two-dimensional object location indicators (e.g., can produce 408); the second deep learning neural network can receive as input the second three-dimensional voxel array and can produce as output, for each of the coronal two-dimensional slices of the second three-dimensional voxel array, a respective one of the set of two-dimensional object location indicators (e.g., can produce 412); and the third deep learning neural network can receive as input the third three-dimensional voxel array and can produce as output, for each of the sagittal two-dimensional slices of the third three-dimensional voxel array, a respective one of the set of two-dimensional object location indicators (e.g., can produce 416).

Although not explicitly shown in FIG. 10, each of the first deep learning neural network, the second deep learning neural network, and the third deep learning neural network can exhibit a modified RetinaNet architecture (e.g., 602) wherein: a ResNet backbone (e.g., 604) of the modified RetinaNet architecture can comprise three-dimensional convolutional kernels instead of two-dimensional convolutional kernels; downsampling operators of the modified RetinaNet architecture can refrain from performing downsampling along a slicing axis; and a Feature Pyramid Network (e.g., 606) of the modified RetinaNet architecture can comprise two-dimensional convolutional kernels instead of three-dimensional convolutional kernels and can be applied, via shared weights, on a slice-wise basis (e.g., as shown with respect to FIG. 6).

Although not explicitly shown in FIG. 10, the deep learning ensemble can comprise a first deep learning neural network (e.g., 402), a second deep learning neural network (e.g., 404), and a third deep learning neural network (e.g., 406) that are in parallel with each other; the at least one three-dimensional voxel array can comprise a single three-dimensional voxel array (e.g., 202) made up of axial two-dimensional slices (e.g., 204); the first deep learning neural network can receive as input the single three-dimensional voxel array and can produce as output, for each of the axial two-dimensional slices of the first three-dimensional voxel array, a respective one of the set of two-dimensional object location indicators (e.g., can produce 408); and the second deep learning neural network and the third deep learning neural network can be idle. Note that this is a mere non-limiting example and that, in other cases, the second or third deep learning neural networks can be executed while the first deep learning neural network remains idle.

Although not explicitly shown in FIG. 10, the deep learning ensemble can generate a set of confidence scores (e.g., 306) respectively corresponding to the set of two-dimensional object location indicators, and can further comprise: rendering, by the device (e.g., via 118) and on an electronic display, a message indicating that the object is present in the at least one three-dimensional voxel array, in response to at least one of the set of confidence scores exceeding a threshold.

Although not explicitly shown in FIG. 10, the deep learning ensemble can generate a set of confidence scores (e.g., 306) respectively corresponding to the set of two-dimensional object location indicators, and can further comprise: rendering, by the device (e.g., via 118) and on an electronic display, one or more of the set of two-dimensional object location indicators that have confidence scores exceeding a threshold.

Although not explicitly shown in FIG. 10, the threshold can be a variable based on user input.

Although not explicitly shown in FIG. 10, the object can be an anatomical structure (e.g., cervical spine or a fracture/injury thereof) of a medical patient.

In various instances, machine learning algorithms or models can be implemented in any suitable way to facilitate any suitable aspects described herein. To facilitate some of the above-described machine learning aspects of various embodiments, consider the following discussion of artificial intelligence (AI). Various embodiments described herein can employ artificial intelligence to facilitate automating one or more features or functionalities. The components can employ various AI-based schemes for carrying out various embodiments/examples disclosed herein. In order to provide for or aid in the numerous determinations (e.g., determine, ascertain, infer, calculate, predict, prognose, estimate, derive, forecast, detect, compute) described herein, components described herein can examine the entirety or a subset of the data to which it is granted access and can provide for reasoning about or determine states of the system or environment from a set of observations as captured via events or data. Determinations can be employed to identify a specific context or action, or can generate a probability distribution over states, for example. The determinations can be probabilistic; that is, the computation of a probability distribution over states of interest based on a consideration of data and events. Determinations can also refer to techniques employed for composing higher-level events from a set of events or data.

Such determinations can result in the construction of new events or actions from a set of observed events or stored event data, whether or not the events are correlated in close temporal proximity, and whether the events and data come from one or several event and data sources. Components disclosed herein can employ various classification (explicitly trained (e.g., via training data) as well as implicitly trained (e.g., via observing behavior, preferences, historical information, receiving extrinsic information, and so on)) schemes or systems (e.g., support vector machines, neural networks, expert systems, Bayesian belief networks, fuzzy logic, data fusion engines, and so on) in connection with performing automatic or determined action in connection with the claimed subject matter. Thus, classification schemes or systems can be used to automatically learn and perform a number of functions, actions, or determinations.

A classifier can map an input attribute vector, $z=(z_1, z_2, z_3, z_4, z_n)$, to a confidence that the input belongs to a class, as by f(z)=confidence(class). Such classification can employ a probabilistic or statistical-based analysis (e.g., factoring into the analysis utilities and costs) to determinate an action to be automatically performed. A support vector machine (SVM) can be an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, or probabilistic classification models providing different patterns of independence, any of which can be employed. Classification as used herein also is inclusive of statistical regression that is utilized to develop models of priority.

Figure 11:
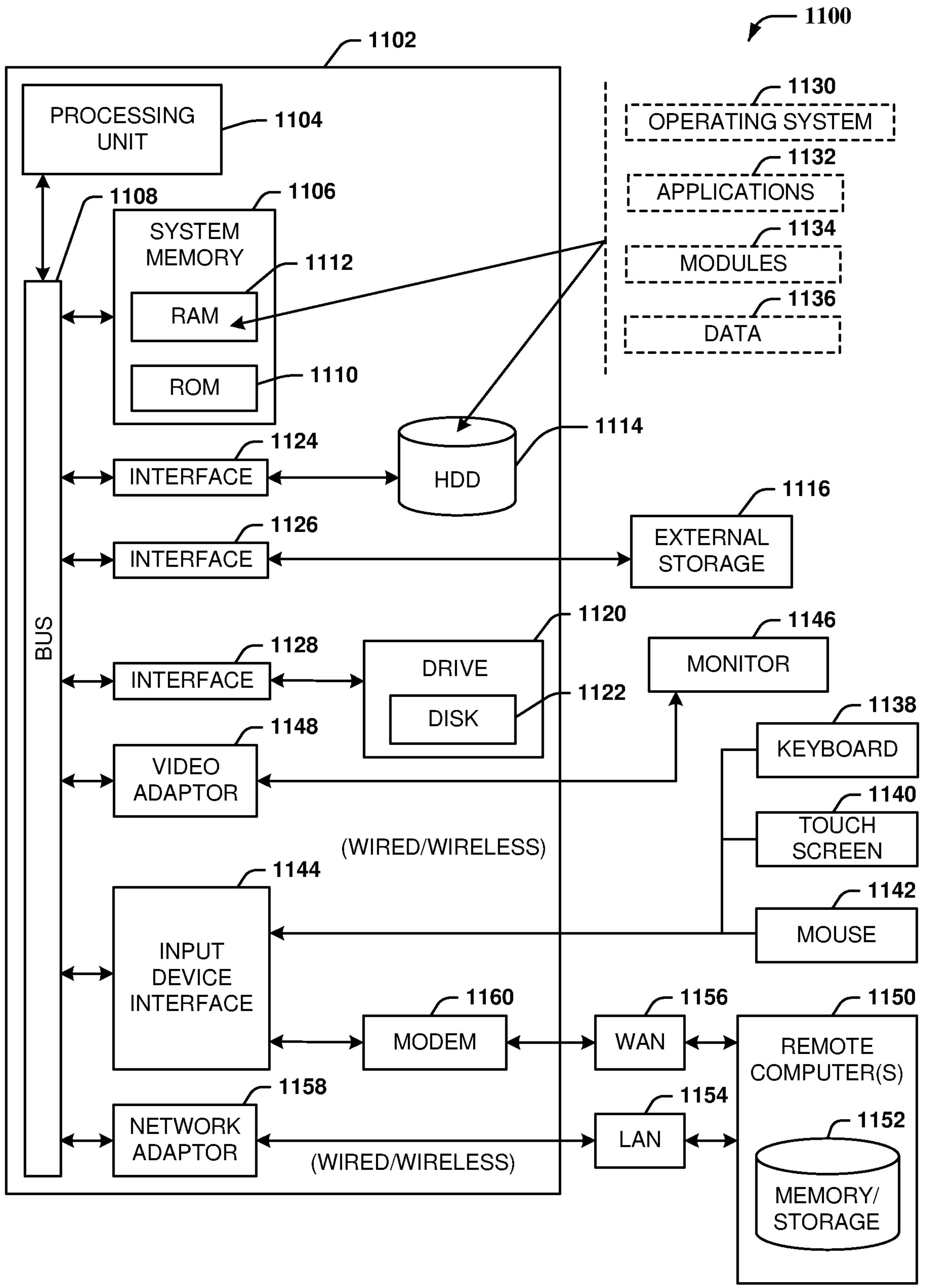
FIG. 11 illustrates a block diagram of an example, non-limiting operating environment in which one or more embodiments described herein can be facilitated.

In order to provide additional context for various embodiments described herein, FIG. 11 and the following discussion are intended to provide a brief, general description of a suitable computing environment 1100 in which the various embodiments of the embodiment described herein can be implemented. While the embodiments have been described above in the general context of computer-executable instructions that can run on one or more computers, those skilled in the art will recognize that the embodiments can be also implemented in combination with other program modules or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multi-processor computer systems, minicomputers, mainframe computers, Internet of Things (IoT) devices, distributed computing systems, as well as personal computers, hand-held computing devices, microprocessor-based or programmable consumer electronics, and the like, each of which can be operatively coupled to one or more associated devices.

The illustrated embodiments of the embodiments herein can be also practiced in distributed computing environments where certain tasks are performed by remote processing devices that are linked through a communications network. In a distributed computing environment, program modules can be located in both local and remote memory storage devices.

Computing devices typically include a variety of media, which can include computer-readable storage media, machine-readable storage media, or communications media, which two terms are used herein differently from one another as follows. Computer-readable storage media or machine-readable storage media can be any available storage media that can be accessed by the computer and includes both volatile and nonvolatile media, removable and non-removable media. By way of example, and not limitation, computer-readable storage media or machine-readable storage media can be implemented in connection with any method or technology for storage of information such as computer-readable or machine-readable instructions, program modules, structured data or unstructured data.

Computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD), Blu-ray disc (BD) or other optical disk storage, magnetic cassettes, magnetic tape, magnetic disk storage or other magnetic storage devices, solid state drives or other solid state storage devices, or other tangible or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 11, the example environment 1100 for implementing various embodiments of the aspects described herein includes a computer 1102, the computer 1102 including a processing unit 1104, a system memory 1106 and a system bus 1108. The system bus 1108 couples system components including, but not limited to, the system memory 1106 to the processing unit 1104. The processing unit 1104 can be any of various commercially available processors. Dual microprocessors and other multi-processor architectures can also be employed as the processing unit 1104.

The system bus 1108 can be any of several types of bus structure that can further interconnect to a memory bus (with or without a memory controller), a peripheral bus, and a local bus using any of a variety of commercially available bus architectures. The system memory 1106 includes ROM 1110 and RAM 1112. A basic input/output system (BIOS) can be stored in a non-volatile memory such as ROM, erasable programmable read only memory (EPROM), EEPROM, which BIOS contains the basic routines that help to transfer information between elements within the computer 1102, such as during startup. The RAM 1112 can also include a high-speed RAM such as static RAM for caching data.

The computer 1102 further includes an internal hard disk drive (HDD) 1114 (e.g., EIDE, SATA), one or more external storage devices 1116 (e.g., a magnetic floppy disk drive (FDD) 1116, a memory stick or flash drive reader, a memory card reader, etc.) and a drive 1120, e.g., such as a solid state drive, an optical disk drive, which can read or write from a disk 1122, such as a CD-ROM disc, a DVD, a BD, etc. Alternatively, where a solid state drive is involved, disk 1122 would not be included, unless separate. While the internal HDD 1114 is illustrated as located within the computer 1102, the internal HDD 1114 can also be configured for external use in a suitable chassis (not shown). Additionally, while not shown in environment 1100, a solid state drive (SSD) could be used in addition to, or in place of, an HDD 1114. The HDD 1114, external storage device(s) 1116 and drive 1120 can be connected to the system bus 1108 by an HDD interface 1124, an external storage interface 1126 and a drive interface 1128, respectively. The interface 1124 for external drive implementations can include at least one or both of Universal Serial Bus (USB) and Institute of Electrical and Electronics Engineers (IEEE) 1394 interface technologies. Other external drive connection technologies are within contemplation of the embodiments described herein.

The drives and their associated computer-readable storage media provide nonvolatile storage of data, data structures, computer-executable instructions, and so forth. For the computer 1102, the drives and storage media accommodate the storage of any data in a suitable digital format. Although the description of computer-readable storage media above refers to respective types of storage devices, it should be appreciated by those skilled in the art that other types of storage media which are readable by a computer, whether presently existing or developed in the future, could also be used in the example operating environment, and further, that any such storage media can contain computer-executable instructions for performing the methods described herein.

A number of program modules can be stored in the drives and RAM 1112, including an operating system 1130, one or more application programs 1132, other program modules 1134 and program data 1136. All or portions of the operating system, applications, modules, or data can also be cached in the RAM 1112. The systems and methods described herein can be implemented utilizing various commercially available operating systems or combinations of operating systems.

Computer 1102 can optionally comprise emulation technologies. For example, a hypervisor (not shown) or other intermediary can emulate a hardware environment for operating system 1130, and the emulated hardware can optionally be different from the hardware illustrated in FIG. 11. In such an embodiment, operating system 1130 can comprise one virtual machine (VM) of multiple VMs hosted at computer 1102. Furthermore, operating system 1130 can provide runtime environments, such as the Java runtime environment or the .NET framework, for applications 1132. Runtime environments are consistent execution environments that allow applications 1132 to run on any operating system that includes the runtime environment. Similarly, operating system 1130 can support containers, and applications 1132 can be in the form of containers, which are lightweight, standalone, executable packages of software that include, e.g., code, runtime, system tools, system libraries and settings for an application.

Further, computer 1102 can be enable with a security module, such as a trusted processing module (TPM). For instance with a TPM, boot components hash next in time boot components, and wait for a match of results to secured values, before loading a next boot component. This process can take place at any layer in the code execution stack of computer 1102, e.g., applied at the application execution level or at the operating system (OS) kernel level, thereby enabling security at any level of code execution.

A user can enter commands and information into the computer 1102 through one or more wired/wireless input devices, e.g., a keyboard 1138, a touch screen 1140, and a pointing device, such as a mouse 1142. Other input devices (not shown) can include a microphone, an infrared (IR) remote control, a radio frequency (RF) remote control, or other remote control, a joystick, a virtual reality controller or virtual reality headset, a game pad, a stylus pen, an image input device, e.g., camera(s), a gesture sensor input device, a vision movement sensor input device, an emotion or facial detection device, a biometric input device, e.g., fingerprint or iris scanner, or the like. These and other input devices are often connected to the processing unit 1104 through an input device interface 1144 that can be coupled to the system bus 1108, but can be connected by other interfaces, such as a parallel port, an IEEE 1394 serial port, a game port, a USB port, an IR interface, a BLUETOOTH® interface, etc.

A monitor 1146 or other type of display device can be also connected to the system bus 1108 via an interface, such as a video adapter 1148. In addition to the monitor 1146, a computer typically includes other peripheral output devices (not shown), such as speakers, printers, etc.

The computer 1102 can operate in a networked environment using logical connections via wired or wireless communications to one or more remote computers, such as a remote computer(s) 1150. The remote computer(s) 1150 can be a workstation, a server computer, a router, a personal computer, portable computer, microprocessor-based entertainment appliance, a peer device or other common network node, and typically includes many or all of the elements described relative to the computer 1102, although, for purposes of brevity, only a memory/storage device 1152 is illustrated. The logical connections depicted include wired/wireless connectivity to a local area network (LAN) 1154 or larger networks, e.g., a wide area network (WAN) 1156. Such LAN and WAN networking environments are commonplace in offices and companies, and facilitate enterprise-wide computer networks, such as intranets, all of which can connect to a global communications network, e.g., the Internet.

When used in a LAN networking environment, the computer 1102 can be connected to the local network 1154 through a wired or wireless communication network interface or adapter 1158. The adapter 1158 can facilitate wired or wireless communication to the LAN 1154, which can also include a wireless access point (AP) disposed thereon for communicating with the adapter 1158 in a wireless mode.

When used in a WAN networking environment, the computer 1102 can include a modem 1160 or can be connected to a communications server on the WAN 1156 via other means for establishing communications over the WAN 1156, such as by way of the Internet. The modem 1160, which can be internal or external and a wired or wireless device, can be connected to the system bus 1108 via the input device interface 1144. In a networked environment, program modules depicted relative to the computer 1102 or portions thereof, can be stored in the remote memory/storage device 1152. It will be appreciated that the network connections shown are example and other means of establishing a communications link between the computers can be used.

When used in either a LAN or WAN networking environment, the computer 1102 can access cloud storage systems or other network-based storage systems in addition to, or in place of, external storage devices 1116 as described above, such as but not limited to a network virtual machine providing one or more aspects of storage or processing of information. Generally, a connection between the computer 1102 and a cloud storage system can be established over a LAN 1154 or WAN 1156 e.g., by the adapter 1158 or modem 1160, respectively. Upon connecting the computer 1102 to an associated cloud storage system, the external storage interface 1126 can, with the aid of the adapter 1158 or modem 1160, manage storage provided by the cloud storage system as it would other types of external storage. For instance, the external storage interface 1126 can be configured to provide access to cloud storage sources as if those sources were physically connected to the computer 1102.

The computer 1102 can be operable to communicate with any wireless devices or entities operatively disposed in wireless communication, e.g., a printer, scanner, desktop or portable computer, portable data assistant, communications satellite, any piece of equipment or location associated with a wirelessly detectable tag (e.g., a kiosk, news stand, store shelf, etc.), and telephone. This can include Wireless Fidelity (Wi-Fi) and BLUETOOTH® wireless technologies. Thus, the communication can be a predefined structure as with a conventional network or simply an ad hoc communication between at least two devices.

Figure 12:
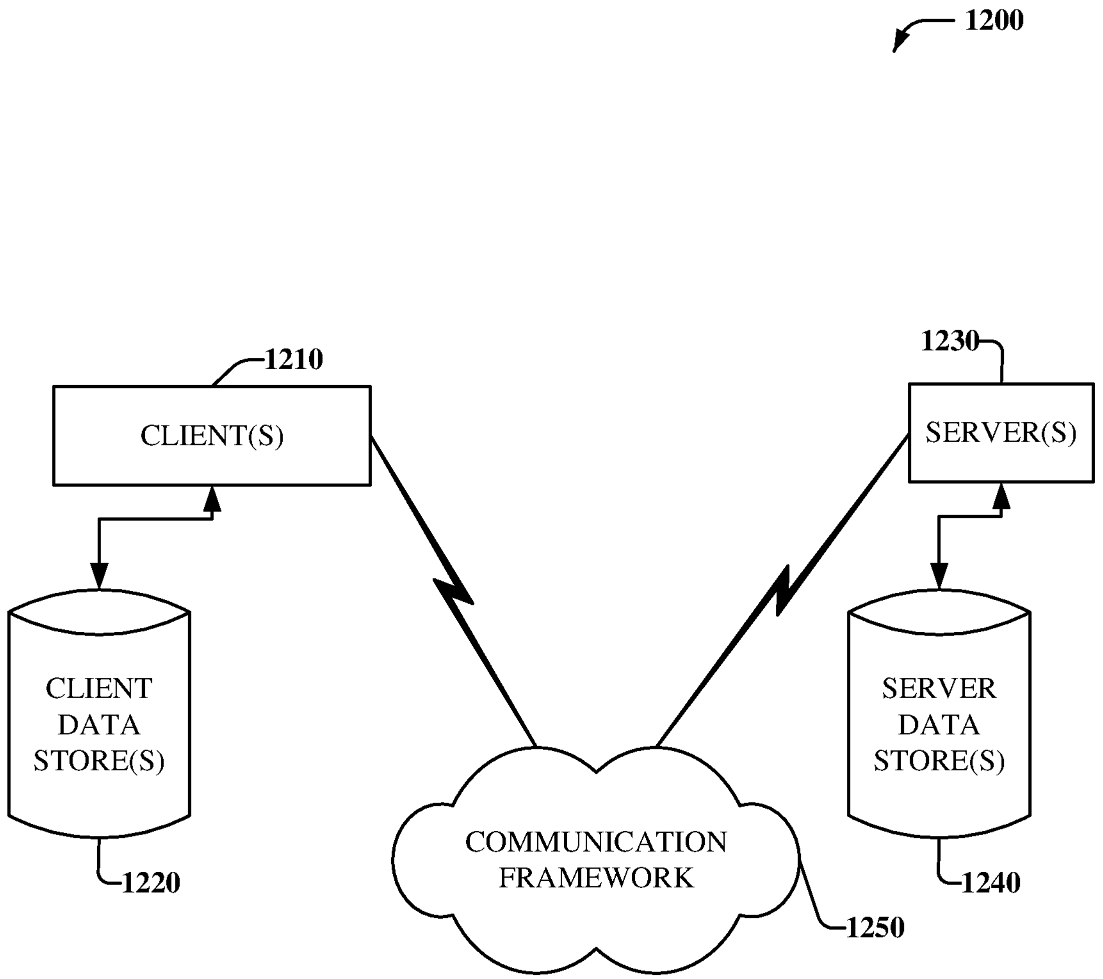
FIG. 12 illustrates an example networking environment operable to execute various implementations described herein.

FIG. 12 is a schematic block diagram of a sample computing environment 1200 with which the disclosed subject matter can interact. The sample computing environment 1200 includes one or more client(s) 1210. The client(s) 1210 can be hardware or software (e.g., threads, processes, computing devices). The sample computing environment 1200 also includes one or more server(s) 1230. The server(s) 1230 can also be hardware or software (e.g., threads, processes, computing devices). The servers 1230 can house threads to perform transformations by employing one or more embodiments as described herein, for example. One possible communication between a client 1210 and a server 1230 can be in the form of a data packet adapted to be transmitted between two or more computer processes. The sample computing environment 1200 includes a communication framework 1250 that can be employed to facilitate communications between the client(s) 1210 and the server(s) 1230. The client(s) 1210 are operably connected to one or more client data store(s) 1220 that can be employed to store information local to the client(s) 1210. Similarly, the server(s) 1230 are operably connected to one or more server data store(s) 1240 that can be employed to store information local to the servers 1230.

Various embodiments may be a system, a method, an apparatus or a computer program product at any possible technical detail level of integration. The computer program product can include a computer readable storage medium (or media) having computer readable program instructions thereon for causing a processor to carry out aspects of various embodiments. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network or a wireless network. The network can comprise copper transmission cables, optical transmission fibers, wireless transmission, routers, firewalls, switches, gateway computers or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of various embodiments can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform various aspects.

Various aspects are described herein with reference to flowchart illustrations or block diagrams of methods, apparatus (systems), and computer program products according to various embodiments. It will be understood that each block of the flowchart illustrations or block diagrams, and combinations of blocks in the flowchart illustrations or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart or block diagram block or blocks. These computer readable program instructions can also be stored in a computer readable storage medium that can direct a computer, a programmable data processing apparatus, or other devices to function in a particular manner, such that the computer readable storage medium having instructions stored therein comprises an article of manufacture including instructions which implement aspects of the function/act specified in the flowchart or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart or block diagram block or blocks.

The flowcharts and block diagrams in the Figures illustrate the architecture, functionality, and operation of possible implementations of systems, methods, and computer program products according to various embodiments. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams or flowchart illustration, and combinations of blocks in the block diagrams or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer or computers, those skilled in the art will recognize that this disclosure also can or can be implemented in combination with other program modules. Generally, program modules include routines, programs, components, data structures, etc. that perform particular tasks or implement particular abstract data types. Moreover, those skilled in the art will appreciate that various aspects can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, or a computer. By way of illustration, both an application running on a server and the server can be a component. One or more components can reside within a process or thread of execution and a component can be localized on one computer or distributed between two or more computers. In another example, respective components can execute from various computer readable media having various data structures stored thereon. The components can communicate via local or remote processes such as in accordance with a signal having one or more data packets (e.g., data from one component interacting with another component in a local system, distributed system, or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. As used herein, the term "and/or" is intended to have the same meaning as "or." Moreover, articles "a" and "an" as used in the subject specification and annexed drawings should generally be construed to mean "one or more" unless specified otherwise or clear from context to be directed to a singular form. As used herein, the terms "example" or "exemplary" are utilized to mean serving as an example, instance, or illustration. For the avoidance of doubt, the subject matter disclosed herein is not limited by such examples. In addition, any aspect or design described herein as an "example" or "exemplary" is not necessarily to be construed as preferred or advantageous over other aspects or designs, nor is it meant to preclude equivalent exemplary structures and techniques known to those of ordinary skill in the art.

The herein disclosure describes non-limiting examples. For ease of description or explanation, various portions of the herein disclosure utilize the term "each," "every," or "all" when discussing various examples. Such usages of the term "each," "every," or "all" are non-limiting. In other words, when the herein disclosure provides a description that is applied to "each," "every," or "all" of some particular object or component, it should be understood that this is a non-limiting example, and it should be further understood that, in various other examples, it can be the case that such description applies to fewer than "each," "every," or "all" of that particular object or component.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:

a processor that executes computer-executable components stored in a non-transitory computer-readable memory, wherein the computer-executable components comprise:

an access component that accesses at least one three-dimensional voxel array; and a model component that localizes, via execution of a deep learning ensemble, an object depicted in the at least one three-dimensional voxel array, wherein the deep learning ensemble receives as input the at least one three-dimensional voxel array, and wherein the deep learning ensemble is configured to:

(i) perform hybrid three-dimensional and two-dimensional convolutional processing on the at least one three-dimensional voxel array, (ii) process the voxel array in a manner that preserves spatial correspondence along a slicing axis by restricting down-sampling operations along the slicing axis, and (iii) produce, as a primary output, a set of two-dimensional object location indicators each indexed to a respective two-dimensional slice of the three-dimensional voxel array, wherein the deep learning ensemble comprises a neural network architecture including a backbone that applies three-dimensional convolutional kernels and a feature pyramid network that applies two-dimensional convolutional kernels on a slice-wise basis using shared weights.

2. The system of claim 1, wherein:

the deep learning ensemble comprises a first deep learning neural network, a second deep learning neural network, and a third deep learning neural network that are in parallel with each other;

the at least one three-dimensional voxel array comprises a first three-dimensional voxel array made up of axial two-dimensional slices, a second three-dimensional voxel array made up of coronal two-dimensional slices, and a third three-dimensional voxel array made up of sagittal two-dimensional slices;

the first deep learning neural network receives as input the first three-dimensional voxel array and produces as output, for each of the axial two-dimensional slices of the first three-dimensional voxel array, a respective one of the set of two-dimensional object location indicators;

the second deep learning neural network receives as input the second three-dimensional voxel array and produces as output, for each of the coronal two-dimensional slices of the second three-dimensional voxel array, a respective one of the set of two-dimensional object location indicators; and the third deep learning neural network receives as input the third three-dimensional voxel array and produces as output, for each of the sagittal two-dimensional slices of the third three-dimensional voxel array, a respective one of the set of two-dimensional object location indicators.

3. The system of claim 2, wherein each of the first deep learning neural network, the second deep learning neural network, and the third deep learning neural network exhibits a modified RetinaNet architecture wherein:

a ResNet backbone of the modified RetinaNet architecture comprises three-dimensional convolutional kernels instead of two-dimensional convolutional kernels;

downsampling operators of the modified RetinaNet architecture do not perform downsampling along a slicing axis; and a Feature Pyramid Network of the modified RetinaNet architecture comprises two-dimensional convolutional kernels instead of three-dimensional convolutional kernels and is applied, via shared weights, on a slice-wise basis.

4. The system of claim 1, wherein:

the deep learning ensemble comprises a first deep learning neural network, a second deep learning neural network, and a third deep learning neural network that are in parallel with each other;

the at least one three-dimensional voxel array comprises a single three-dimensional voxel array made up of axial two-dimensional slices;

the first deep learning neural network receives as input the single three-dimensional voxel array and produces as output, for each of the axial two-dimensional slices of the single three-dimensional voxel array, a respective one of the set of two-dimensional object location indicators; and the second deep learning neural network and the third deep learning neural network are idle.

5. The system of claim 1, wherein the deep learning ensemble generates a set of confidence scores respectively corresponding to the set of two-dimensional object location indicators, and wherein the computer-executable components further comprise:

a display component that renders, on an electronic display, a message indicating that the object is present in the at least one three-dimensional voxel array, in response to at least one of the set of confidence scores exceeding a threshold.

6. The system of claim 1, wherein the deep learning ensemble generates a set of confidence scores respectively corresponding to the set of two-dimensional object location indicators, and wherein the computer-executable components further comprise:

a display component that renders, on an electronic display, one or more of the set of two-dimensional object location indicators that have confidence scores exceeding a threshold.

7. The system of claim 6, wherein the threshold is a variable based on user input.

8. The system of claim 1, wherein the object is an anatomical structure of a medical patient.

9. A computer-implemented method, comprising:

accessing, by a device operatively coupled to a processor, at least one three-dimensional voxel array; and executing, by the device, a deep learning ensemble, to localize an object depicted in the at least one three-dimensional voxel array, wherein the deep learning ensemble:

(i) applies hybrid three-dimensional and two-dimensional convolutional operations to the three-dimensional voxel array;

(ii) performs the convolutional operations in a manner that maintains spatial correspondence of voxel data along a slicing axis of the three-dimensional voxel array by restricting down-sampling operations along the slicing axis; and (iii) generates, as a primary result of the executing, a plurality of two-dimensional object location indicators, each object location indicator being associated with a respective two-dimensional slice of the three-dimensional voxel array;

wherein the deep learning ensemble comprises a neural network architecture including a backbone that applies three-dimensional convolutional kernels and a feature pyramid network that applies two-dimensional convolutional kernels on a slice-wise basis using shared weights.

10. The computer-implemented method of claim 9, wherein:

the deep learning ensemble comprises a first deep learning neural network, a second deep learning neural network, and a third deep learning neural network that are in parallel with each other;

the at least one three-dimensional voxel array comprises a first three-dimensional voxel array made up of axial two-dimensional slices, a second three-dimensional voxel array made up of coronal two-dimensional slices, and a third three-dimensional voxel array made up of sagittal two-dimensional slices;

the first deep learning neural network receives as input the first three-dimensional voxel array and produces as output, for each of the axial two-dimensional slices of the first three-dimensional voxel array, a respective one of the set of two-dimensional object location indicators;

the second deep learning neural network receives as input the second three-dimensional voxel array and produces as output, for each of the coronal two-dimensional slices of the second three-dimensional voxel array, a respective one of the set of two-dimensional object location indicators; and the third deep learning neural network receives as input the third three-dimensional voxel array and produces as output, for each of the sagittal two-dimensional slices of the third three-dimensional voxel array, a respective one of the set of two-dimensional object location indicators.

11. The computer-implemented method of claim 10, wherein each of the first deep learning neural network, the second deep learning neural network, and the third deep learning neural network exhibits a modified RetinaNet architecture wherein:

a ResNet backbone of the modified RetinaNet architecture comprises three-dimensional convolutional kernels instead of two-dimensional convolutional kernels;

downsampling operators of the modified RetinaNet architecture do not perform downsampling along a slicing axis; and a Feature Pyramid Network of the modified RetinaNet architecture comprises two-dimensional convolutional kernels instead of three-dimensional convolutional kernels and is applied, via shared weights, on a slice-wise basis.

12. The computer-implemented method of claim 9, wherein:

the deep learning ensemble comprises a first deep learning neural network, a second deep learning neural network, and a third deep learning neural network that are in parallel with each other;

the at least one three-dimensional voxel array comprises a single three-dimensional voxel array made up of axial two-dimensional slices;

the first deep learning neural network receives as input the single three-dimensional voxel array and produces as output, for each of the axial two-dimensional slices of the single three-dimensional voxel array, a respective one of the set of two-dimensional object location indicators; and the second deep learning neural network and the third deep learning neural network are idle.

13. The computer-implemented method of claim 9, wherein the deep learning ensemble generates a set of confidence scores respectively corresponding to the set of two-dimensional object location indicators, and further comprising:

rendering, by the device and on an electronic display, a message indicating that the object is present in the at least one three-dimensional voxel array, in response to at least one of the set of confidence scores exceeding a threshold.

14. The computer-implemented method of claim 9, wherein the deep learning ensemble generates a set of confidence scores respectively corresponding to the set of two-dimensional object location indicators, and further comprising:

rendering, by the device and on an electronic display, one or more of the set of two-dimensional object location indicators that have confidence scores exceeding a threshold.

15. The computer-implemented method of claim 14, wherein the threshold is a variable based on user input.

16. The computer-implemented method of claim 9, wherein the object is an anatomical structure of a medical patient.

17. A computer program product for facilitating hybrid 3D-to-2D slice-wise object localization ensembles, the computer program product comprising a computer-readable memory having program instructions embodied therewith, the program instructions executable by a processor to cause the processor to:

access at least one three-dimensional voxel array depicting a cervical spine of a medical patient; and localize, via execution of a deep learning ensemble, the program instructions cause the processor to:

(i) perform hybrid three-dimensional and two-dimensional convolutional processing on the three-dimensional voxel array;

(ii) process voxel data in a manner that preserves spatial correspondence along a slicing axis of the three-dimensional voxel array by restricting downsampling operations along the slicing axis; and (iii) generate, as a primary localization result, a set of two-dimensional fracture location indicators, each fracture location indicator being indexed to a respective two-dimensional slice of the three-dimensional voxel array;

wherein the deep learning ensemble comprises a neural network architecture including a backbone that applies three-dimensional convolutional kernels and a feature pyramid network that applies two-dimensional convolutional kernels on a slice-wise basis using shared weights.

18. The computer program product of claim 17, wherein:

the deep learning ensemble comprises a first deep learning neural network, a second deep learning neural network, and a third deep learning neural network that are in parallel with each other;

the at least one three-dimensional voxel array comprises a first three-dimensional voxel array made up of axial two-dimensional slices, a second three-dimensional voxel array made up of coronal two-dimensional slices, and a third three-dimensional voxel array made up of sagittal two-dimensional slices;

the first deep learning neural network receives as input the first three-dimensional voxel array and produces as output, for each of the axial two-dimensional slices of the first three-dimensional voxel array, a respective one of the set of two-dimensional fracture location indicators;

the second deep learning neural network receives as input the second three-dimensional voxel array and produces as output, for each of the coronal two-dimensional slices of the second three-dimensional voxel array, a respective one of the set of two-dimensional fracture location indicators; and the third deep learning neural network receives as input the third three-dimensional voxel array and produces as output, for each of the sagittal two-dimensional slices of the third three-dimensional voxel array, a respective one of the set of two-dimensional fracture location indicators.

19. The computer program product of claim 18, wherein each of the first deep learning neural network, the second deep learning neural network, and the third deep learning neural network exhibits a modified RetinaNet architecture wherein:

a ResNet backbone of the modified RetinaNet architecture comprises three-dimensional convolutional kernels instead of two-dimensional convolutional kernels;

downsampling operators of the modified RetinaNet architecture do not perform downsampling along a slicing axis; and a Feature Pyramid Network of the modified RetinaNet architecture comprises two-dimensional convolutional kernels instead of three-dimensional convolutional kernels and is applied, via shared weights, on a slice-wise basis.

20. The computer program product of claim 17, wherein:

the deep learning ensemble comprises a first deep learning neural network, a second deep learning neural network, and a third deep learning neural network that are in parallel with each other;

the at least one three-dimensional voxel array comprises a single three-dimensional voxel array made up of axial two-dimensional slices;

the first deep learning neural network receives as input the single three-dimensional voxel array and produces as output, for each of the axial two-dimensional slices of the single three-dimensional voxel array, a respective one of the set of two-dimensional fracture location indicators; and the second deep learning neural network and the third deep learning neural network are idle.

* * * * *